(12) United States Patent
Davies et al.

(10) Patent No.: US 12,011,210 B2
(45) Date of Patent: Jun. 18, 2024

(54) ELECTROSURGICAL DEVICE HAVING A DISTAL APERTURE

(71) Applicant: Boston Scientific Medical Device Limited, Ballybrit (IE)

(72) Inventors: Gareth Davies, Toronto (CA); John Paul Urbanski, Toronto (CA); Ellen Harfield, Rockwood (CA); Mahmood Mirza, Toronto (CA); Yun Uhm, Toronto (CA); Linus Leung, Toronto (CA); Ferryl Alley, Devonshire (BM)

(73) Assignee: Boston Scientific Medical Device Limited, Ballybrit (IE)

( * ) Notice: Subject to any disclaimer, the term of this patent is extended or adjusted under 35 U.S.C. 154(b) by 53 days.

(21) Appl. No.: 16/423,092

(22) Filed: May 27, 2019

(65) Prior Publication Data
US 2019/0274754 A1 Sep. 12, 2019

Related U.S. Application Data

(63) Continuation of application No. 15/262,715, filed on Sep. 12, 2016, now Pat. No. 11,020,173, which is a
(Continued)

(51) Int. Cl.
*A61B 18/14* (2006.01)
*A61B 18/00* (2006.01)
(Continued)

(52) U.S. Cl.
CPC ............ *A61B 18/1477* (2013.01); *A61B 2018/00077* (2013.01); *A61B 2018/00083* (2013.01);
(Continued)

(58) Field of Classification Search
CPC .............. A61B 2018/1425; A61B 2018/1427
See application file for complete search history.

(56) References Cited

U.S. PATENT DOCUMENTS

| 175,254 A | 3/1876 | Oberly |
|---|---|---|
| 827,626 A | 7/1906 | Gillet |

(Continued)

FOREIGN PATENT DOCUMENTS

| EP | 0651974 A2 | 5/1995 |
|---|---|---|
| JP | 07-504594 A | 5/1995 |

(Continued)

OTHER PUBLICATIONS

International Search Report and Written Opinion received for PCT Patent Application No. PCT/IB2014/064600, dated Dec. 31, 2014, 17 pages.
(Continued)

*Primary Examiner* — Ronald Hupczey, Jr.
(74) *Attorney, Agent, or Firm* — Nelson Mullins Riley & Scarborough LLP

(57) ABSTRACT

A method and apparatus are disclosed for providing forward fluid delivery through an electrosurgical device, while avoiding coring when energy is delivered to the electrosurgical device. The device has a distal face defining an opening, with the distal face including at least one cutting portion and at least one non-cutting portion. An embodiment of the electrosurgical device for puncturing tissue includes an elongate member defining a lumen for fluid; a distal portion including an electrode and the distal face which defines at least one aperture. The portion of the at least one cutting portion defines a leading portion partially surrounding a circumference of the at least one aperture wherein the outer diameter of the at least one of the distal portion of the electrosurgical device or the electrode decreases towards a distal tip of the electrosurgical device.

13 Claims, 15 Drawing Sheets

Related U.S. Application Data continuation-in-part of application No. PCT/IB2014/064600, filed on Sep. 17, 2014, which is a continuation-in-part of application No. PCT/IB2014/059641, filed on Mar. 11, 2014, said application No. 15/262,715 is a continuation-in-part of application No. 14/850,545, filed on Sep. 10, 2015, now Pat. No. 10,751,115, which is a continuation-in-part of application No. PCT/IB2014/059641, filed on Mar. 11, 2014.

(60) Provisional application No. 61/787,617, filed on Mar. 15, 2013.

(51) Int. Cl.
  *A61B 18/02* (2006.01)
  *A61B 90/00* (2016.01)
  *A61B 18/12* (2006.01)

(52) U.S. Cl.
  CPC .............. *A61B 2018/00297* (2013.01); *A61B 2018/00351* (2013.01); *A61B 2018/00601* (2013.01); *A61B 18/1206* (2013.01); *A61B 2018/1412* (2013.01); *A61B 2018/1427* (2013.01); *A61B 2018/1467* (2013.01); *A61B 2018/1497* (2013.01); *A61B 2090/392* (2016.02); *A61B 2090/3966* (2016.02); *A61B 2218/002* (2013.01)

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,674,499 A * | 6/1987 | Pao .................... A61B 18/1402 604/20 |
| 4,682,596 A * | 7/1987 | Bales ................. A61B 18/1492 606/45 |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,221,281 A | 6/1993 | Klicek |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,520,685 A * | 5/1996 | Wojciechowicz .......................... A61B 18/1402 606/49 |
| 5,530,685 A | 6/1996 | Katayama et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,925,045 A | 7/1999 | Reimels et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,968,042 A | 10/1999 | Ernster |
| 5,972,416 A | 10/1999 | Reimels et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |

(56) References Cited

U.S. PATENT DOCUMENTS

| | | | |
|---|---|---|---|
| 6,053,870 A | 4/2000 | Fulton, III | |
| 6,053,904 A | 4/2000 | Scribner et al. | |
| 6,056,747 A | 5/2000 | Saadat et al. | |
| 6,063,093 A | 5/2000 | Winston et al. | |
| 6,093,185 A | 7/2000 | Ellis et al. | |
| 6,106,515 A | 8/2000 | Winston et al. | |
| 6,106,520 A | 8/2000 | Aufer et al. | |
| 6,117,131 A | 9/2000 | Taylor | |
| 6,142,992 A | 11/2000 | Cheng et al. | |
| 6,142,996 A * | 11/2000 | Mirhashemi | A61B 18/1402 606/41 |
| 6,146,380 A | 11/2000 | Racz et al. | |
| 6,155,264 A | 12/2000 | Ressemann et al. | |
| 6,156,031 A | 12/2000 | Aita et al. | |
| 6,171,305 B1 | 1/2001 | Sherman | |
| 6,179,824 B1 | 1/2001 | Eggers et al. | |
| 6,193,676 B1 | 2/2001 | Winston et al. | |
| 6,193,715 B1 | 2/2001 | Wrublewski et al. | |
| 6,210,408 B1 | 4/2001 | Chandrasekaran et al. | |
| 6,217,575 B1 | 4/2001 | Devore et al. | |
| 6,221,061 B1 | 4/2001 | Engelson et al. | |
| 6,228,076 B1 | 5/2001 | Winston et al. | |
| 6,245,054 B1 | 6/2001 | Fuimaono et al. | |
| 6,267,758 B1 | 7/2001 | Daw et al. | |
| 6,283,983 B1 | 9/2001 | Makower et al. | |
| 6,292,678 B1 | 9/2001 | Hall et al. | |
| 6,293,945 B1 | 9/2001 | Parins et al. | |
| 6,296,615 B1 | 10/2001 | Brockway et al. | |
| 6,296,636 B1 | 10/2001 | Cheng et al. | |
| 6,302,898 B1 | 10/2001 | Edwards et al. | |
| 6,304,769 B1 | 10/2001 | Arenson et al. | |
| 6,315,777 B1 | 11/2001 | Comben | |
| 6,328,699 B1 | 12/2001 | Eigler et al. | |
| 6,360,128 B2 | 3/2002 | Kordis et al. | |
| 6,364,877 B1 | 4/2002 | Goble et al. | |
| 6,379,350 B1 * | 4/2002 | Sharkey | A61B 18/1402 606/49 |
| 6,385,472 B1 | 5/2002 | Hall et al. | |
| 6,394,976 B1 | 5/2002 | Winston et al. | |
| 6,395,002 B1 | 5/2002 | Ellman et al. | |
| 6,419,674 B1 | 7/2002 | Bowser et al. | |
| 6,428,551 B1 | 8/2002 | Hall et al. | |
| 6,450,989 B2 | 9/2002 | Dubrul et al. | |
| 6,475,214 B1 | 11/2002 | Moaddeb | |
| 6,482,202 B1 | 11/2002 | Goble et al. | |
| 6,485,485 B1 | 11/2002 | Winston et al. | |
| 6,508,754 B1 | 1/2003 | Liprie et al. | |
| 6,524,303 B1 | 2/2003 | Garibaldi | |
| 6,530,923 B1 | 3/2003 | Dubrul et al. | |
| 6,554,827 B2 | 4/2003 | Chandrasekaran et al. | |
| 6,562,031 B2 | 5/2003 | Chandrasekaran et al. | |
| 6,562,049 B1 | 5/2003 | Norlander et al. | |
| 6,565,562 B1 | 5/2003 | Shah et al. | |
| 6,589,240 B2 | 7/2003 | Hinchliffe | |
| 6,607,529 B1 | 8/2003 | Jones et al. | |
| 6,632,222 B1 | 10/2003 | Edwards et al. | |
| 6,639,999 B1 | 10/2003 | Cookingham et al. | |
| 6,650,923 B1 | 11/2003 | Lesh et al. | |
| 6,651,672 B2 | 11/2003 | Roth | |
| 6,662,034 B2 | 12/2003 | Segner et al. | |
| 6,663,621 B1 | 12/2003 | Winston et al. | |
| 6,702,811 B2 | 3/2004 | Stewart et al. | |
| 6,709,444 B1 | 3/2004 | Makower | |
| 6,723,052 B2 | 4/2004 | Mills | |
| 6,733,511 B2 | 5/2004 | Hall et al. | |
| 6,740,103 B2 | 5/2004 | Hall et al. | |
| 6,752,800 B1 | 6/2004 | Winston et al. | |
| 6,755,816 B2 | 6/2004 | Ritter et al. | |
| 6,811,544 B2 | 11/2004 | Schaer | |
| 6,814,733 B2 | 11/2004 | Schwartz et al. | |
| 6,820,614 B2 | 11/2004 | Bonutti | |
| 6,834,201 B2 | 12/2004 | Gillies et al. | |
| 6,842,639 B1 | 1/2005 | Winston et al. | |
| 6,852,109 B2 | 2/2005 | Winston et al. | |
| 6,855,143 B2 | 2/2005 | Davison et al. | |
| 6,860,856 B2 | 3/2005 | Ward et al. | |
| 6,869,431 B2 | 3/2005 | Maguire et al. | |
| 6,911,026 B1 | 6/2005 | Hall et al. | |
| 6,951,554 B2 | 10/2005 | Johansen et al. | |
| 6,951,555 B1 | 10/2005 | Suresh et al. | |
| 6,955,675 B2 | 10/2005 | Jain | |
| 6,970,732 B2 | 11/2005 | Winston et al. | |
| 6,980,843 B2 | 12/2005 | Eng et al. | |
| 7,029,470 B2 | 4/2006 | Francischelli et al. | |
| 7,056,294 B2 | 6/2006 | Khairkhahan et al. | |
| 7,083,566 B2 | 8/2006 | Tornes et al. | |
| 7,112,197 B2 | 9/2006 | Hartley et al. | |
| 7,169,148 B2 | 1/2007 | O'Halloran | |
| 7,335,197 B2 | 2/2008 | Sage et al. | |
| 7,618,430 B2 | 11/2009 | Scheib | |
| 7,651,482 B2 * | 1/2010 | Harris | A61M 5/3286 604/272 |
| 7,651,492 B2 | 1/2010 | Wham | |
| 7,666,203 B2 | 2/2010 | Chanduszko et al. | |
| 7,678,081 B2 | 3/2010 | Whiting et al. | |
| 7,682,360 B2 | 3/2010 | Guerra | |
| 7,828,796 B2 | 11/2010 | Wong et al. | |
| 7,883,515 B2 | 2/2011 | Kear | |
| 7,900,928 B2 | 3/2011 | Held et al. | |
| 8,182,480 B2 | 5/2012 | Huseman | |
| 8,187,272 B2 | 5/2012 | Sensenbrenner et al. | |
| 8,192,425 B2 | 6/2012 | Mirza et al. | |
| 8,257,323 B2 | 9/2012 | Joseph et al. | |
| 8,388,549 B2 | 3/2013 | Paul et al. | |
| 8,500,697 B2 | 8/2013 | Kurth et al. | |
| 11,339,579 B1 | 5/2022 | Stearns | |
| 2001/0012934 A1 | 8/2001 | Chandrasekaran et al. | |
| 2001/0021867 A1 | 9/2001 | Kordis et al. | |
| 2002/0019644 A1 | 2/2002 | Hastings et al. | |
| 2002/0022781 A1 | 2/2002 | McIntire et al. | |
| 2002/0022836 A1 | 2/2002 | Goble et al. | |
| 2002/0035361 A1 | 3/2002 | Houser et al. | |
| 2002/0049438 A1 | 4/2002 | Sharkey et al. | |
| 2002/0087153 A1 | 7/2002 | Roschak et al. | |
| 2002/0087156 A1 | 7/2002 | Maguire et al. | |
| 2002/0111608 A1 | 8/2002 | Baerveldt et al. | |
| 2002/0111618 A1 | 8/2002 | Stewart et al. | |
| 2002/0123749 A1 | 9/2002 | Jain | |
| 2002/0147485 A1 | 10/2002 | Mamo et al. | |
| 2002/0169377 A1 | 11/2002 | Khairkhahan et al. | |
| 2002/0188302 A1 | 12/2002 | Berg et al. | |
| 2002/0198521 A1 | 12/2002 | Maguire | |
| 2003/0032929 A1 | 2/2003 | McGuckin | |
| 2003/0040742 A1 | 2/2003 | Underwood et al. | |
| 2003/0144658 A1 | 7/2003 | Schwartz et al. | |
| 2003/0158480 A1 | 8/2003 | Tornes et al. | |
| 2003/0163153 A1 | 8/2003 | Scheib | |
| 2003/0225392 A1 | 12/2003 | McMichael et al. | |
| 2004/0015162 A1 | 1/2004 | McGaffigan | |
| 2004/0024396 A1 | 2/2004 | Eggers | |
| 2004/0030328 A1 | 2/2004 | Eggers et al. | |
| 2004/0044350 A1 | 3/2004 | Martin et al. | |
| 2004/0073243 A1 | 4/2004 | Sepetka et al. | |
| 2004/0077948 A1 | 4/2004 | Violante et al. | |
| 2004/0116851 A1 | 6/2004 | Johansen et al. | |
| 2004/0127963 A1 | 7/2004 | Uchida et al. | |
| 2004/0133113 A1 | 7/2004 | Krishnan | |
| 2004/0133130 A1 | 7/2004 | Ferry et al. | |
| 2004/0143256 A1 | 7/2004 | Bednarek | |
| 2004/0147950 A1 | 7/2004 | Mueller et al. | |
| 2004/0181213 A1 | 9/2004 | Gondo | |
| 2004/0230188 A1 | 11/2004 | Cioanta et al. | |
| 2005/0004585 A1 | 1/2005 | Hall et al. | |
| 2005/0010208 A1 | 1/2005 | Winston et al. | |
| 2005/0049628 A1 | 3/2005 | Schweikert et al. | |
| 2005/0059966 A1 | 3/2005 | McClurken et al. | |
| 2005/0065507 A1 | 3/2005 | Hartley et al. | |
| 2005/0085806 A1 | 4/2005 | Auge et al. | |
| 2005/0096529 A1 | 5/2005 | Cooper et al. | |
| 2005/0101984 A1 | 5/2005 | Chanduszko et al. | |
| 2005/0119556 A1 | 6/2005 | Gillies et al. | |
| 2005/0137527 A1 | 6/2005 | Kunin | |
| 2005/0149012 A1 | 7/2005 | Penny et al. | |
| 2005/0203504 A1 | 9/2005 | Wham et al. | |

(56) References Cited

U.S. PATENT DOCUMENTS

| | | |
|---|---|---|
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0178646 A1 | 8/2006 | Harris et al. |
| 2006/0178666 A1 | 8/2006 | Cosman et al. |
| 2006/0189972 A1 | 8/2006 | Grossman |
| 2006/0189979 A1 | 8/2006 | Esch et al. |
| 2006/0224156 A1 | 10/2006 | Arts et al. |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0005053 A1 | 1/2007 | Dando |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0086121 A1 | 4/2008 | Sensenbrenner et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0221567 A1 | 9/2008 | Sixto et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0057074 A1 | 3/2010 | Roman et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0028970 A1 | 2/2011 | Woloszko et al. |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2011/0202056 A1 | 8/2011 | Sartor |
| 2012/0172857 A1 | 7/2012 | Harrison et al. |
| 2012/0232546 A1 | 9/2012 | Mirza et al. |
| 2012/0265055 A1 | 10/2012 | Melsheimer et al. |
| 2012/0271334 A1 | 10/2012 | Pless et al. |
| 2012/0330156 A1 | 12/2012 | Brown et al. |
| 2013/0046305 A1 | 2/2013 | Davies |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2013/0303997 A1 | 11/2013 | Kimmel et al. |
| 2013/0304036 A1 | 11/2013 | Kimmel et al. |
| 2013/0304051 A1 | 11/2013 | Kimmel et al. |
| 2014/0012228 A1 | 1/2014 | Jabba et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

FOREIGN PATENT DOCUMENTS

| | | | |
|---|---|---|---|
| JP | 2009-131565 A | 6/2009 | |
| JP | 2012-090999 A | 5/2012 | |
| WO | 2001/024720 A1 | 4/2001 | |
| WO | 02/56805 A2 | 7/2002 | |
| WO | 2005/046739 A2 | 5/2005 | |
| WO | WO-2010135793 A1 * | 12/2010 | ......... A61B 18/1477 |
| WO | 2011/146243 A1 | 11/2011 | |

OTHER PUBLICATIONS

International Search Report for International Application No. PCT/IB2014/059641 with International Filing Date Mar. 11, 2014 dated Jun. 27, 2014.

Japanese Search Report for counterpart to parent Japanese Application No. 2015-562485, dated Jan. 26, 2018.

Patent Cooperation Treaty, International Preliminary Report on Patentability, International Application No. PCT/IB2014/059641, dated Sep. 15, 2015.

Patent Cooperation Treaty, International Preliminary Report on Patentability, International Application No. PCT/IB2014/064600, dated Sep. 13, 2016.

Supplementary European Search Report for European Application No. 14763885.2, dated Sep. 28, 2016.

Supplementary European Search Report for European Application No. 14885380.7, dated Oct. 18, 2017.

* cited by examiner

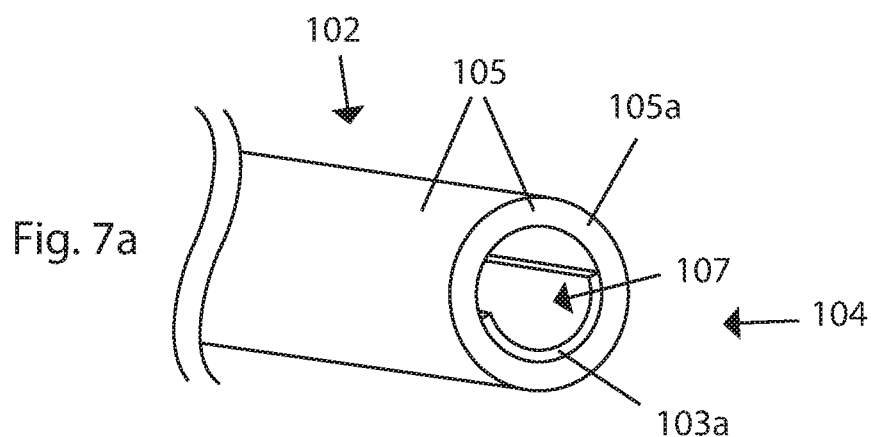
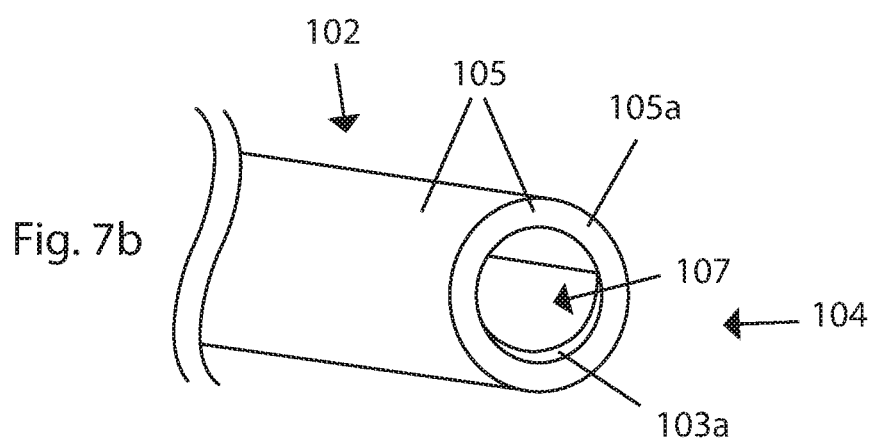
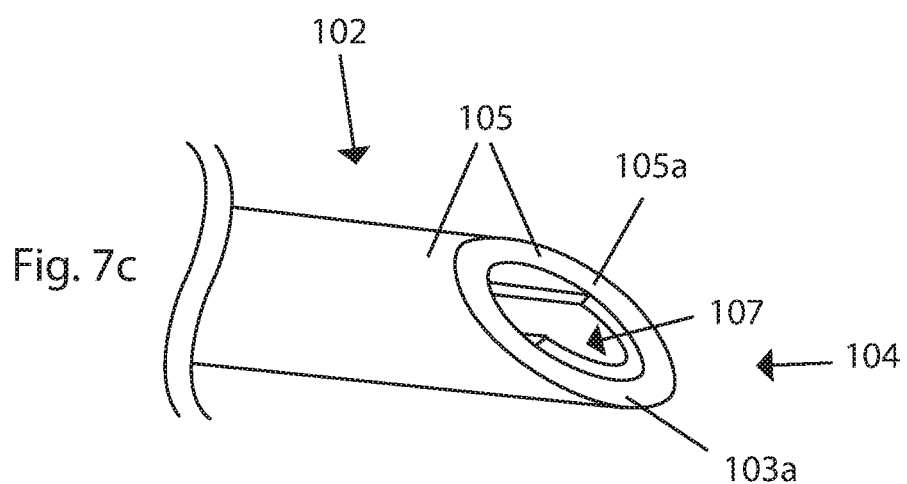

ELECTROSURGICAL DEVICE HAVING A DISTAL APERTURE

TECHNICAL FIELD

The disclosure relates to methods and devices usable to deliver energy within the body of a patient. More specifically, the present invention is concerned with an electrosurgical perforation apparatus.

SUMMARY

Disclosed herein are embodiments of a surgical device providing an elongate (non-circular) puncture, dilation, and forward fluid delivery, while avoiding coring; the device generally comprises a distal face defining an opening, the distal face of the device including at least one elongate cutting portion and at least one non-cutting portion.

In one broad aspect, embodiments of the present invention include an electrosurgical device for puncturing tissue comprising an elongate member defining a lumen for receiving a fluid; a distal face defining at least one aperture; and the distal face including at least one cutting portion and at least one non-cutting portion cooperating to produce an elongated cut in a tissue when electrical energy is delivered to the distal face while avoiding coring of the tissue.

As a feature of this aspect, some embodiments include the at least one cutting portion is substantially arcuate and is located along an inner surface of the elongate member.

As another feature of this aspect, some embodiments include a distal end the elongate member being asymmetrically truncated to define a stepped distal face having a leading portion and a recessed portion, the leading portion comprising the at least one cutting portion, and the recessed portion comprising the at least one non-cutting portion.

As another feature of this aspect, some embodiments further comprise a protruding electrode defining a leading surface distal of the elongate member, the leading surface including the at least one cutting portion.

As another feature of this aspect, some embodiments include the at least one cutting portion being arcuate and partially surrounding the aperture, the at least one cutting portion comprising at least one active electrode and at least one return electrode being operable for bi-polar energy delivery.

As yet another feature of this aspect, some embodiments include the at least one cutting portion comprising an active electrode and a return electrode parallel to one another and substantially extending across the aperture, the active electrode and the return electrode being operable for bi-polar energy delivery.

As another feature of this aspect, some embodiments include the elongate member comprising an electrically conductive tubular member at least partially covered by electrically insulating material, wherein the at least one non-cutting portion of the distal face comprises a layer of electrical insulation.

As another feature of this aspect, some embodiments include the elongate member comprising an electrically conductive tubular member at least partially covered by electrically insulating material, the electrically conductive tubular member having a cut away portion proximal of the distal face, and the electrosurgical device further comprising an electrically insulating insert located in the cut away portion, wherein the distal face of the electrosurgical device comprises a distal surface of the tubular member defining the at least one cutting portion and a distal surface of the electrically insulating insert defining at least a portion of the at least one non-cutting portion.

In another broad aspect, embodiments of the present invention include an electrosurgical device for puncturing tissue comprising an elongate member comprising an electrically non-conductive material and defining a lumen for receiving a fluid; a distal face defining an aperture; and the distal face including at least one cutting portion and at least one non-cutting portion configured for cooperating to produce an elongated cut in a tissue when electrical energy is delivered to the distal face, while avoiding coring of the tissue.

In another broad aspect, embodiments of the present invention include an electrosurgical device for puncturing tissue comprising an elongate member defining a lumen for receiving a fluid; and a distal surface of the elongate member defining an aperture and an electrically conductive portion at least partially surrounding the aperture, the electrically conductive portion defining a biased electrode configured to produce a non-coring cut in tissue when energy is delivered to the distal surface.

BRIEF DESCRIPTION OF THE DRAWINGS

In order that the invention may be readily understood, embodiments of the invention are illustrated by way of examples in the accompanying drawings, in which:

FIGS. 7a-c are illustrations of embodiments of a device with an off-center elongate curved electrode;

DETAILED DESCRIPTION

Figure 1:
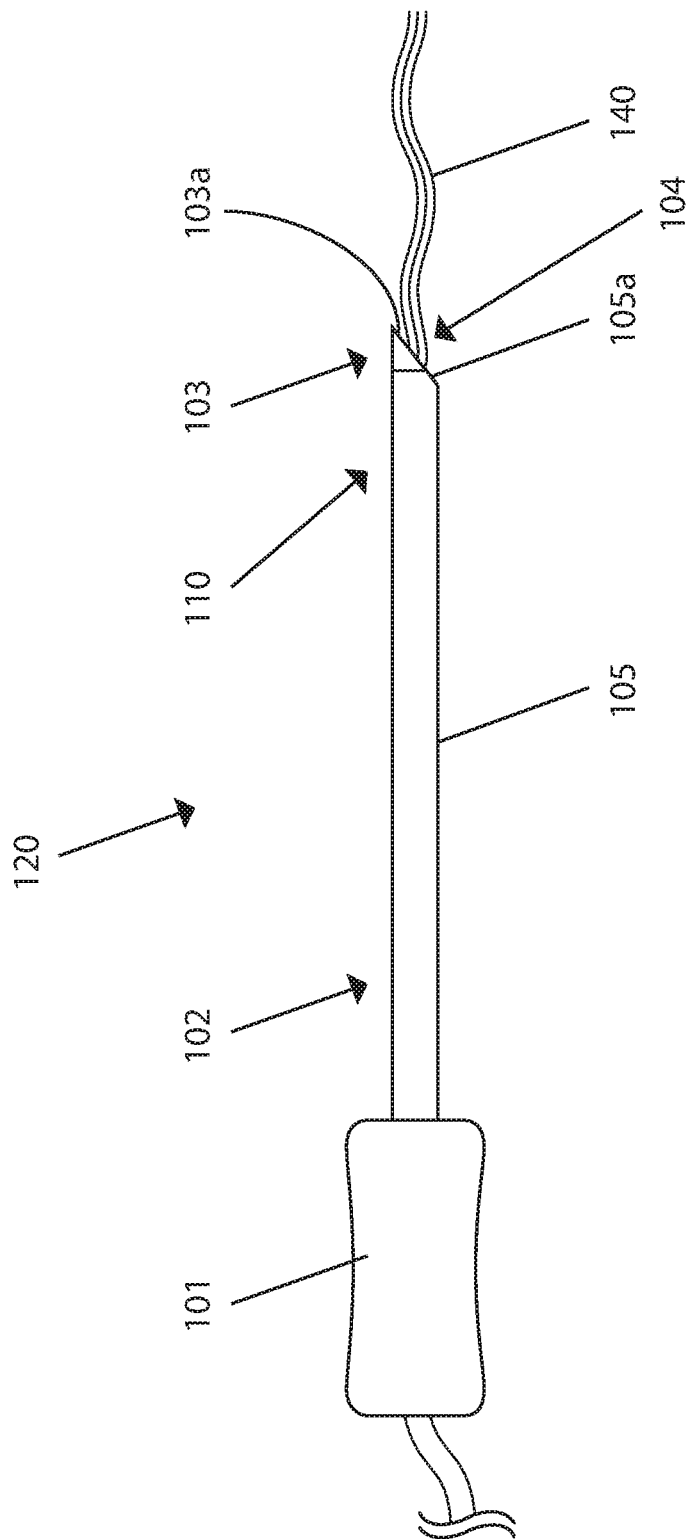
FIG. 1 is an illustration of an embodiment of a device including a handle and shaft.

Devices used for puncturing tissue, for example transseptal tissue of a patient's heart, are typically either mechanical or electrosurgical in nature. Some electrosurgical devices incorporate side-ports and do not have a forward facing lumen aperture, and consequently lack the ability, for example, to effectively inject fluid or monitor fluid pressure when confined inside of a close-fitting dilator lumen. In addition, while it is possible in some cases for a guide-wire to be passed through or to be received by a side-port, in general, devices lacking a forward facing aperture do not facilitate the use of a guide-wire with the device. In contrast, devices with a forward facing aperture are typically more effective in injecting fluid, monitoring pressure, and typically better facilitate usage of a guide-wire than a side-port device.

A conventional Brockenbrough transseptal needle with a sharp beveled tip has a forward facing aperture that may be used for injecting fluid or monitoring pressure. However, conventional transseptal needles typically utilize mechanical force to puncture tissue, which is not effective at puncturing tissue under certain circumstances. To meet the challenge of puncturing through a tissue that does not facilitate being mechanically punctured, some physicians have used an electrocautery generator or the like to electrify the mechanical needle and to thereby produce an ad hoc electrosurgical device with a forward facing aperture. One drawback to electrifying a Brockenbrough needle is the risk of tissue coring. A core (or plug) of tissue is typically cut from surrounding tissue upon delivery of energy and is subsequently captured in the lumen of the electrosurgical device upon advancement of the needle through tissue. The tissue core may be released from the lumen by flushing, potentially leading to emboli and increasing the risk of a stroke or some other ischemic event. Furthermore, a non-insulated and electrified Brockenbrough needle bears an additional increased risk of burns to the patient and physician.

This disclosure includes different embodiments of an electrosurgical device that has a distal face for creating an elongate initial puncture that is configured to be dilated when the device is advanced while reducing the risks of tissue coring and emboli formation. Embodiments of the device also have a forward facing lumen aperture to provide for pressure monitoring, forward fluid delivery, and to facilitate being used with a guide-wire.

In typical embodiments, the distal surface of an electrode defines at least one elongate portion (when seen from the end view), whereby the device creates a puncture corresponding with the at least one elongate portion thereby defining one or more flaps of tissue which the distal face of the device may push aside when the device is advanced. The term elongate electrode is used to describe electrodes that are non-circular and that may be described as being longer in one dimension than in another. In some embodiments, the distal surface of the electrode defines an elongate shape which is generally C-shaped, U-shaped, semicircular-shaped, shaped like a segment of a circle, shaped like an arc of a circle, arcuate, crescent-shaped, rectangular-shaped, generally straight, or star-shaped (i.e. having segments radiating from a central point). Some embodiments have a pair of generally parallel electrodes which are generally straight (or rectangular-shaped) and operable for bi-polar delivery of energy. While this disclosure describes electrosurgical devices that are generally circular in cross-section, the concepts and claims of this disclosure also apply to non-circular devices e.g. square-shaped, elliptical-shaped. Furthermore, some embodiments are configured such that an electrode used for puncturing tissue does not completely encircle or enclose a forward facing lumen aperture, thereby avoiding having a ring-shaped electrode that may possibly core tissue.

Thus, the present inventors have conceived and reduced to practice a surgical device for puncturing tissue, such as an atrial septum of a heart, wherein the surgical device allows for forward fluid delivery for staining the septum and has less risk of coring tissue relative to an electrified Brockenbrough needle or similar device. The device comprises a distal face defining at least one aperture, with the distal face including at least one cutting portion and at least one non-cutting portion cooperating to produce an elongated cut in a tissue when electrical energy is delivered to the distal face, while avoiding coring of the tissue. Typical embodiments can be advanced over a guide-wire to a treatment site.

With specific reference now to the drawings in detail, it is stressed that the particulars shown are by way of example and for purposes of illustrative discussion of certain embodiments of the present invention only. Before explaining embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 4A:
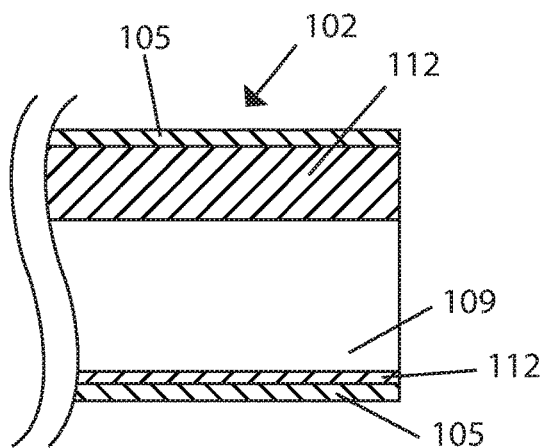
FIGS. 4a-g are illustrations of embodiments of a device with an off center lumen.
Figure 4B:
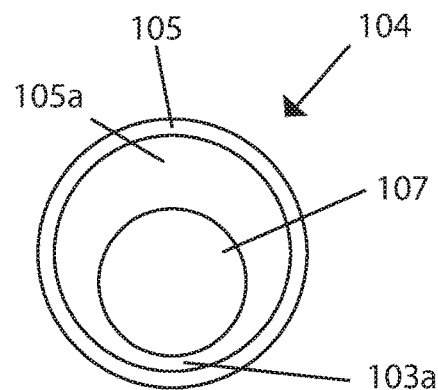

FIG. 1 is an illustration of an embodiment of a device including a handle and shaft. Electrosurgical device 120 of FIG. 1 is comprised of elongate member 102, electrically insulating material 105 and distal portion 110. The handle 101 is mechanically coupled to the proximal end of the elongate member 102. Elongate member 102 defines a lumen (FIG. 4a). Distal portion 110 includes electrode 103 and distal face 104 (further described herein below) which defines an aperture. The embodiment is operable to direct a fluid forward, as represented by fluid flow lines 140. The forward facing aperture facilitates the device being used with a guide-wire.

Some embodiments of electrosurgical device 120 include electrically insulating material 105 covering portions of the shaft of elongate member 102 and/or distal face 104 of the device. The insulating material is understood by one skilled in the art to be an effective insulator, which may be a 100 percent insulating material or a partially insulating material. In the case of a layer of partially insulating material being located on distal face 104, the partially insulating material functions as an effective insulator, when the device is used, by only allowing limited electrical energy flow through the partially insulating material, such that there is insufficient electrical energy to heat adjacent tissue to create a void in the tissue for advancing the electrosurgical device through.

In general, in this disclosure, the term "distal face" is with reference to the entire electrosurgical device and used to refer to the end surfaces of the device seen from the distal end view (not interior or side surfaces). The term "distal surface" is used to refer to the end surfaces seen from the distal end for a particular part of the device. In some embodiments, the distal surface of elongate member 102 and the distal face 104 refer to the same surface, for example, the embodiment of FIG. 3a.

Various embodiments of this disclosure include an electrosurgical device 120 for puncturing tissue comprising: an elongate member 102 defining a lumen 109 for receiving a fluid; with distal face 104 of the electrosurgical device defining at least one aperture 107; and the distal face 104 including at least one cutting portion 103a and at least one non-cutting portion 105a cooperating to produce an elongated cut in a tissue when electrical energy is delivered to the distal face 104 while avoiding coring of the tissue. Some embodiments only have one distal aperture, while other embodiments have more than one aperture. In some examples, the device can be described as having an aperture that is divided into more than one portion.

Various embodiments of this disclosure further include at least one cutting portion 103a being configured to create an initial partial puncture upon energy delivery, the initial partial puncture substantially corresponding to the at least one cutting portion. The "initial partial puncture" is a puncture created by energy delivery before the tissue is dilated or pushed aside when the electrosurgical device is advanced after energy delivery; the initial partial puncture is too small to receive the device without dilating or pushing aside tissue. As previously noted, distal face 104 is configured for advancing while avoiding coring tissue during advancement of elongate member 102. The initial puncture is dilated by distal face 104 of electrosurgical device 120 as the device is advanced; if the shaft of the elongate member is tapered there is typically further dilation by the shaft during advancement.

In some embodiments, elongate member 102 has a length of about 30 cm to about 100 cm to facilitate the puncture of a septum of a heart. In some embodiments, the elongate member has an outer diameter of about 0.40 mm to about 1.5 mm to minimize hemodynamic stability, for example, by ensuring that the perforation will not cause hemodynamic instability once electrosurgical device 120 is removed. In some embodiments, the electrosurgical device 120 is a stiff elongate needle.

Some embodiments of electrosurgical device 120 include an elongate member 102 having flexural rigidity of at least about 0.016 $Nm^2$, for example a flexural rigidity of about 0.017 $Nm^2$, to provide tactile feedback for a user of the device.

Some embodiments of the device have markers for highlighting the location of important landmarks on electrosurgical device 120. Such landmarks may include the location where the elongated member 102 begins to curve, the location of the electrode 103, or the location of the proximal edge of a beveled distal face. In some embodiments the marker is radiopaque. Imaging markers may be different shapes including, but not limited to, a ring-shaped hollow band or a coil. Alternative embodiments include imaging markers that are disc-shaped, rectangular, and elongate, that define other geometric shapes, or that define symbols.

An elongate member 102, which can be comprised of one or more layers/components of plastic, other polymers, metal, or other materials, may have a marker embedded in its sidewall which may be either all metal or substantially (mostly) metal. For example, the marker receiving sidewall can be covered with a relatively thin layer of polymer, such as the sidewall being covered with a layer of electrical insulation. As all metals are radiopaque to some degree, a radiopaque marker should be more radiopaque than the metal comprising the elongate member to function properly. In general, for any embodiment of the device having a radiopaque marker, the radiopaque marker may be comprised of a material that is more radiopaque than whatever material elongate member 102 is comprised of.

While the embodiment of FIG. 1 has a generally straight elongate member 102, in alternative embodiments, the elongate member comprises a curved section. In some examples, the curved section has a curve length of from about 10 to about 25 cm and traverses from about 20° to about 40° of a circle. In some other examples, the curved section has a curve length of from about 4 to about 7 cm and traverses from about 70 degrees to about 110 degrees of a circle.

Typically, handle 101 comprises a connector for receiving an electrical plug or other electrical connector, and a fluid port for receiving a second connector, for example, a luer lock. Electrical energy may be delivered from an energy source, through the connector and, typically, a wire (not shown in the drawing) located within handle 101. The electrical energy is then conveyed to the elongate member 102 and electrode 103.

Some embodiments of the handle 101 include a relatively large graspable surface having ridges so that tactile feedback can be transmitted relatively efficiently, for example by transmitting vibrations.

In some embodiments, one end of a tubing is operatively coupled to a source of fluid (not shown in drawing), for example a syringe, pump, intravenous fluid bag, etc., and the other end of the tubing is operatively coupled with a connector to a fluid port of handle 101 which is in fluid communication with lumen 109 of elongate member 102 via a conduit in the handle (not shown), whereby the tubing and lumen 109 are in fluid communication with one another, thus allowing for a flow of fluid between an external device and lumen 109.

In some embodiments, aperture 107 and the lumen 109 (e.g. FIG. 8) together provide a pressure transmitting lumen which is coupled to the external tubing by a connector, and the tubing is in fluid communication with a pressure sensing device, for example, a pressure transducer.

Figure 2A:
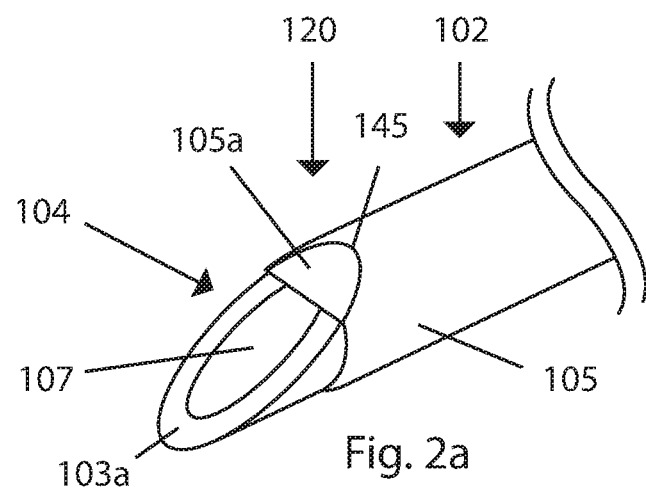
FIGS. 2a-c are illustrations of an embodiment of a device with an electrically conductive tubular member and insulation.
Figure 2B:
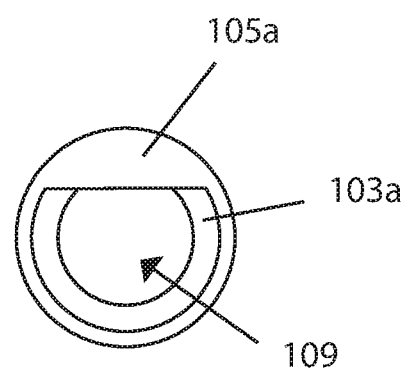
Figure 2C:
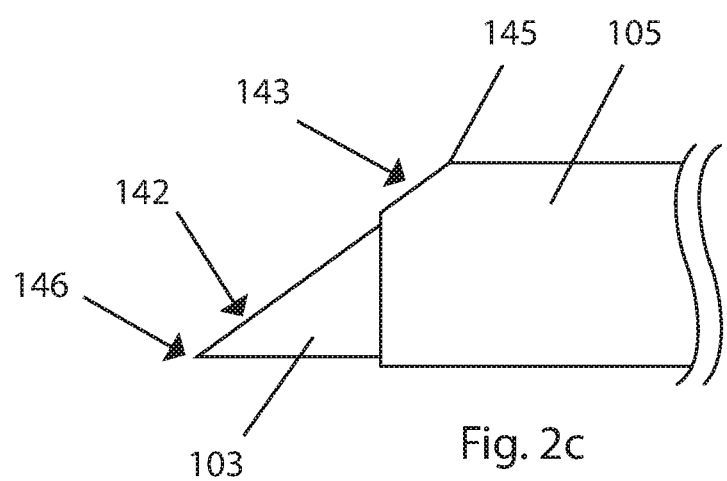

FIGS. 2a to 2c illustrate the distal portion of an embodiment of an electrosurgical device 120 in which elongate member 102 is an electrically conductive tubular member. Elongate member 102 defines a lumen 109 for receiving a fluid. The fluid within the lumen (FIG. 2b) may be injected, withdrawn, or may remain substantially stationary. In some embodiments, the electrically conductive tubular member is comprised of stainless steel.

The electrically conductive tubular member is at least partially covered by electrically insulating material 105 with a distal portion of the electrically conductive tubular member uncovered (i.e. electrically exposed) to define electrode 103. The non-cutting portion 105a of the distal face comprises a layer of electrical insulation, which in some embodiments (e.g. FIGS. 2a to c), is the same as the electrically insulating material 105 covering the shaft of the tubular member, which includes both the electrically insulating material 105 covering the shaft of the tubular member extending over the distal face 104 and the electrical insulation covering the distal face 104 being the same type of material applied separately. In alternative embodiments, the layer of electrical insulation covering distal face 104 is a different type of insulation.

Distal face 104 of the electrosurgical device defines an aperture 107 which is in communication with lumen 109. Referring to FIG. 2b, the layer of electrical insulation (non-cutting portion 105a) has the shape of a segment of a circle whereby the electrically conductive tubular member (cutting portion 103a of FIG. 2b) and the layer of electrical insulation define aperture 107.

In the embodiment of FIGS. 2a to c, distal face 104 is beveled and is comprised of an electrically exposed and conductive cutting portion 103a and an electrically insulated non-cutting portion 105a. The distal surface of electrode 103 forms cutting portion 103a which, in this embodiment, is generally C-shaped or arcuate shaped when viewing the distal face 104 from a distal end-view. Cutting portion 103a is elongate i.e. it is non-circular and has a length greater than its width. Furthermore, cutting portion 103a does not completely encircle, circumscribe or enclose aperture 107 but rather partially surrounds the aperture.

The proximal portion 143 of distal face 104 (FIG. 2c) is comprised of non-cutting portion 105a. Electrically insulated portion 105a extends from a periphery 145 of distal face 104 to partially cover the end surface of the tubular member. In some embodiments, non-cutting portion 105a is comprised of polymer insulation, which may be a heat shrink, a spray coating, or a material selectively coated by vapor deposition. In some alternative embodiments, non-cutting portion 105a comprises a ceramic. In some embodiments, the distal face of the electrically conductive tubular member has a step recess wherein a layer of insulation is received to thereby provide for a planar distal face 104 (i.e. to avoid having a stepped surface).

The cutting portion 103a is configured such that, when the electrosurgical device is advanced into a tissue, energy delivered by the electrically exposed cutting portion 103a punctures the tissue without the tissue substantially occluding lumen 109. In particular, it is the leading surface of electrode 103 that defines the cutting surface of the electrode (i.e. cutting portion 103a) which actually cuts into tissue when the energy delivery device is advanced while delivering energy. The outer perimeter of the distal surface of electrode 103 defines a portion (but not all) of the perimeter of distal face 104 (FIG. 2a), whereby the device creates a puncture corresponding with a portion (but not all) of the perimeter of the distal face 104, such that the puncture defines a flap of tissue which the beveled distal face pushes aside as the device is advanced.

The embodiment of electrosurgical device 120 of FIG. 2c includes a distal tip 146 which is substantially rounded or atraumatic, as it is not necessary to have a sharp tip on the device for puncturing. The rounded tip reduces the risk of accidental tissue puncture and skiving of supporting dilators. In other words, the distal portion 142 of the distal face is substantially rounded. In some alternative embodiments, the tip of the device is sharp. Furthermore, the planar surface of distal face 104 is substantially atraumatic.

While in the embodiment of FIGS. 2a to c, the distal face is beveled, in some alternative embodiments the distal face comprises a flat tip. In such embodiments, the configuration of the distal face allows electrosurgical device 120 to be operable to electrically puncture and push aside tissue without coring, as the device is advanced.

FIGS. 3a to d illustrate embodiments of electrosurgical device 120 wherein an electrically conductive material forms cutting portion 103a and non-cutting portion 105a comprises an electrically insulative coating 106 on the distal face of the device. In each of FIGS. 3a to d the distal surface of elongate member 102 includes one cutting portion 103a and one non-cutting portion 105a. Alternative embodiments contain more than one cutting portion 103a and/or more than one non-cutting portion 105a. In some embodiments the electrically insulative coating 106 comprises a non-polymeric layer of a material selected from the group including oxides, nitrides and ceramics. More specific examples include the layer of material being a metal oxide, silicon oxide, silicon dioxide, or diamond thin film. In other embodiments, the electrically insulative coating 106 may be any solid state insulating material.

In some embodiments elongate member 102 comprises an electrically conductive tubular member (e.g. stainless steel), and the at least one non-cutting portion 105a comprises the electrically insulating material positioned along a portion of a distal surface of the elongate member 102, and furthermore an electrically exposed portion of the distal surface of the elongate member 102 forms the at least one cutting portion 103a. Such embodiments may be produced by a layer of electrically insulative oxide being deposited upon an electrically conductive metal tube by methods including (but not limited to) evaporation, chemical vapor deposition, or sputtering. This layer can be deposited on only the distal surface of the tube or it can also be deposited on the side of the tube. A portion, or portions, of the electrically insulative coating 106 is removed by methods including (but not limited to) laser ablation, chemical etching or plasma etching to form the at least one cutting portion 103a. Alternatively, masking can be used to cover the at least one cutting portion 103a during the deposition process and the masking removed after deposition to expose the electrode, while the rest of the distal surface is covered with insulative material to form at least one non-cutting portion 105a.

Figure 3A:
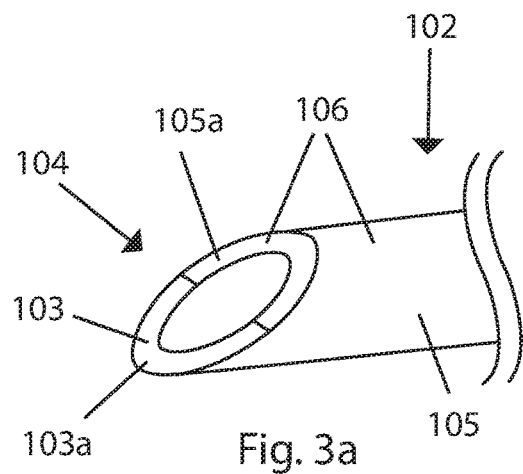
FIGS. 3a-d are illustrations of embodiments of a device with electrically non-conductive coatings on its distal face.
Figure 3B:
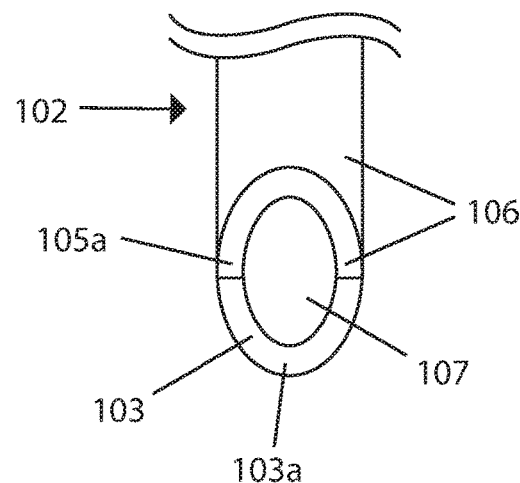
Figure 3C:
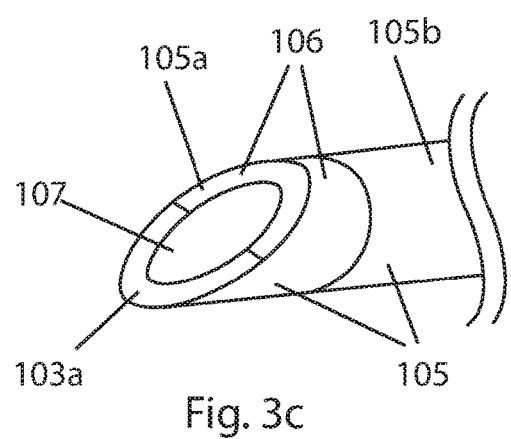
Figure 3D:
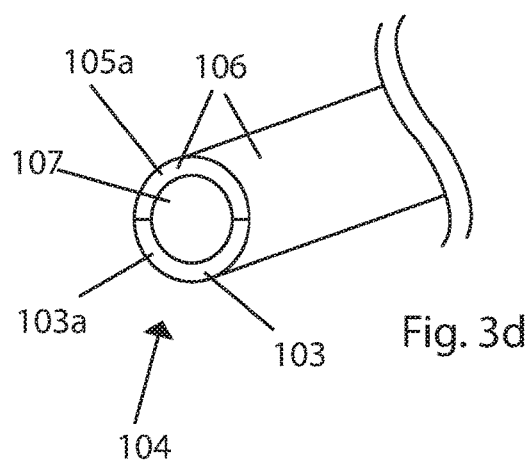

FIGS. 3a and 3b are side and front perspective views, respectively, of an electrosurgical device 120 wherein the distal face 104 comprises a beveled surface. Non-cutting portion 105a and electrical insulation 105 (on the shaft of elongate member 102) are both comprised of the electrically insulative coating 106. Cutting portion 103a is comprised of the distal surface of electrode 103. In the embodiment of FIG. 3c, the distal portion of the electrically insulating material 105 on the shaft of elongate member 102 is comprised of the electrically insulative coating 106 (described above) and the proximal portion is comprised of polymer 105b. In the embodiment of FIG. 3d, the distal face 104 of the device comprises a substantially flat tip.

In some alternative embodiments, the at least one cutting portion is located on the distal face 104 along an inner surface of the elongate member 102 i.e. the cutting portion 103a is adjacent aperture 107 while not extending to the outer periphery of the distal face 104.

Non-polymeric coatings disclosed above (e.g. ceramics, oxides, and diamond thin film) can function as effective insulators in thinner layers than typical polymers. In some examples of electrosurgical device 120, the electrically insulative coating comprises a layer less than about 1 micron thick. In some specific examples, the electrically insulative coating comprises a layer from about 100 nanometers to about 1 micron thick. In some other examples, the electrically insulative coating comprises a layer about 1 micron to about 50 microns thick. In some specific examples, the electrically insulative coating comprises a layer about 1 micron to about 25 microns thick, and some more specific examples, the electrically insulative coating comprises a layer about 1 micron to about 10 microns thick.

In some alternative embodiments, wherein the at least one cutting portion comprises an electrically conductive material, the at least one non-cutting portion of the distal face is comprised of a partially electrically insulating layer. A flow of electricity through an electrode that causes enough tissue heating to puncture tissue electrically (i.e. without a pushing force), when applied to an effective partially insulating layer on distal face 104 of the device, results in some electrical flow through the partially insulating layer, but it is insufficient to heat the tissue to create a void in the tissue for advancing the electrosurgical device through.

FIGS. 4a to g are for an electrosurgical device 120 for puncturing tissue comprising an elongate member 102 defining a lumen 109 (FIG. 4a) for receiving a fluid. A distal surface of the elongate member 102 defines an aperture 107 and an electrically conductive portion (the distal surface of electrode 103) at least partially surrounding the aperture. The electrically conductive portion defines a biased electrode 103 structured to produce a non-coring cut in tissue when energy is delivered to the distal surface. The distal surface includes a non-cutting portion 105a and a cutting portion 103a, as to be explained below. Furthermore, the distal surface of the elongate member 102 is configured for advancing while avoiding coring during advancement of the elongate member.

Figure 4C:
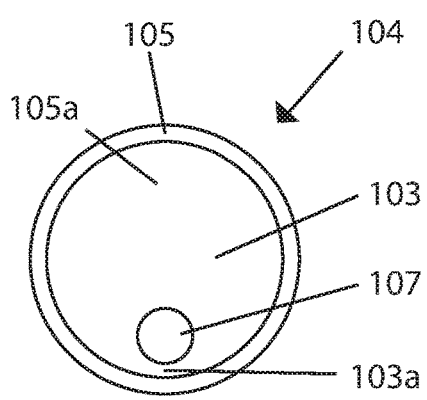

FIGS. 4a to d show embodiments having an electrically conductive elongate member 102 having a layer of electrically insulating material 105 covering the shaft of the elongate member. In the example of FIG. 4c, the distal surface of elongate member 102 is indicated by electrode 103 (which is also the electrically conductive portion), and the distal face 104 of electrosurgical device 120 includes electrically insulating material 105. The embodiment of FIG. 4e includes a distal face 104 wherein the electrically insulating material 105 extends over a portion of the electrode 103.

In typical embodiments, wherein the aperture is off center, the electrically conductive portion (electrode 103) defines an outer perimeter, and a narrow region of the electrically conductive portion includes the part of the outer perimeter which is closest to the aperture (e.g. the bottom of electrode 103 in FIG. 4c) and a wide region of the electrically conductive portion includes the part of the outer perimeter which is furthest from the aperture (e.g. the top of electrode 103 in FIG. 4c), to thereby define, respectively, a narrow conductive region and a wide conductive region.

When electrical power is supplied to the distal surface of the electrically conductive portion, the voltage is the same for the narrow and wide conductive regions, while the electrical field strength and electrical flow is more concentrated through the narrow conductive region into adjacent tissue than through the wide conductive region, whereby tissue adjacent the narrow conductive region heats to a higher temperature than tissue adjacent the wide conductive region. As an example, in some cases, the tissue adjacent the wide conductive region heats to 50 degrees Celsius, which does not electrically perforate tissue, while the tissue adjacent at least a portion of narrow conductive region heats to 300 degrees Celsius, which does electrically perforate tissue. Consequently, having the electrically conductive portion configured to provide a greater concentration of electrical flow through the narrow conductive region than through the wide conductive region defines a biased electrode wherein the narrow conductive region includes at least some of the cutting portion 103a and the wide conductive region includes at least some of the non-cutting portion 105a.

Some alternative embodiments includes elongate member 102 being substantially comprised of a non-conductive material. In the example of FIGS. 4f and g, electrosurgical device 120 includes an elongate member comprised of electrically insulating material 105 (typically a polymer), and a wire 111 operable to supply electricity to an electrode 103. Electrode 103 has the general configuration of a plate and is comprised of an electrically conductive material, for example, metal. It has no sharp corners or edges to prevent the formation of hot spots caused by discontinuities. In the embodiment of FIGS. 4f and g, electrode 103 covers the end surface of the electrically insulating material 105 such that the distal surface of electrode 103 forms the distal face 104 of electrosurgical device 120. Some embodiments include at least a part of the narrow conductive region is arcuate-shaped. In the example of FIG. 4g, the part of the narrow conductive region which is arcuate-shaped includes a portion having a substantially constant radial width or thickness.

Figure 4D:
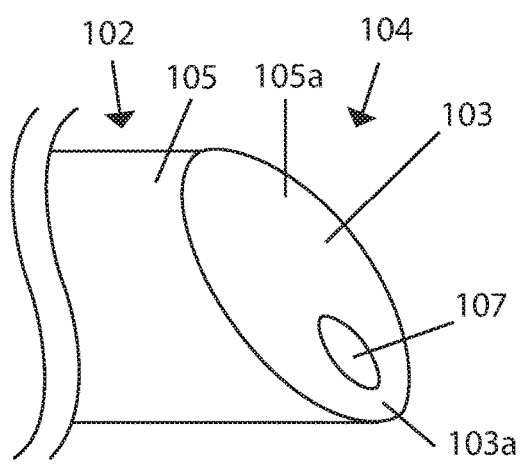
Figure 4E:
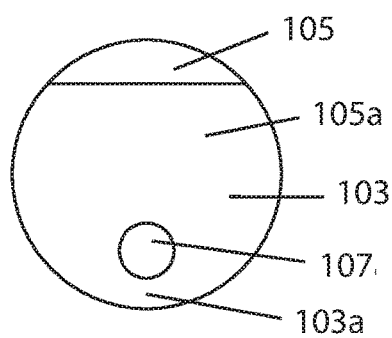
Figure 4F:
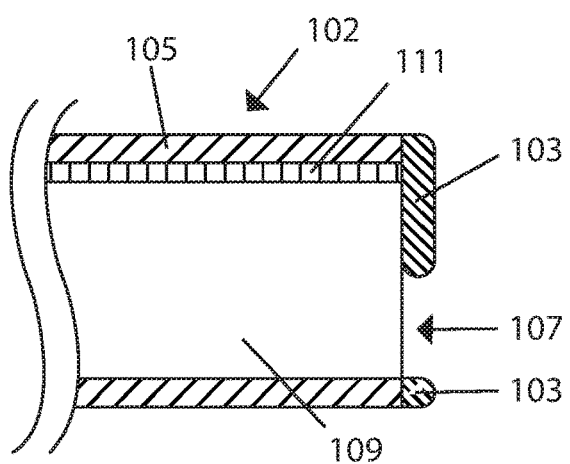
Figure 4G:
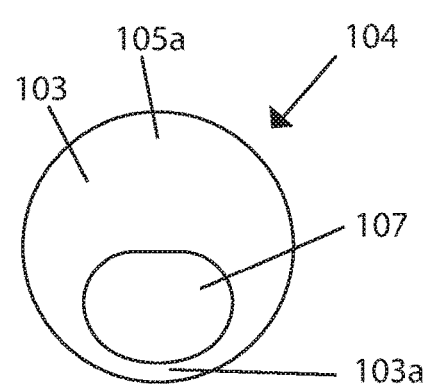

The embodiment of FIG. 4d has a distal face 104 which is beveled, while the embodiment of FIGS. 4a and f each have a distal face 104 comprising a substantially flat surfaced tip.

Figure 5A:
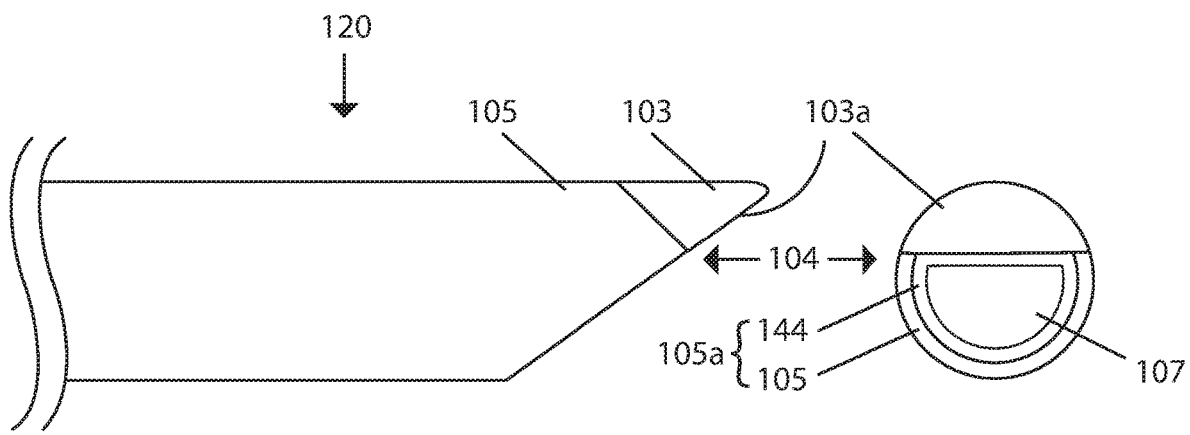
FIGS. 5a to 5c are illustrations of an embodiment in which an electrically conductive tubular member receives an electrically insulating insert.
Figure 5B:
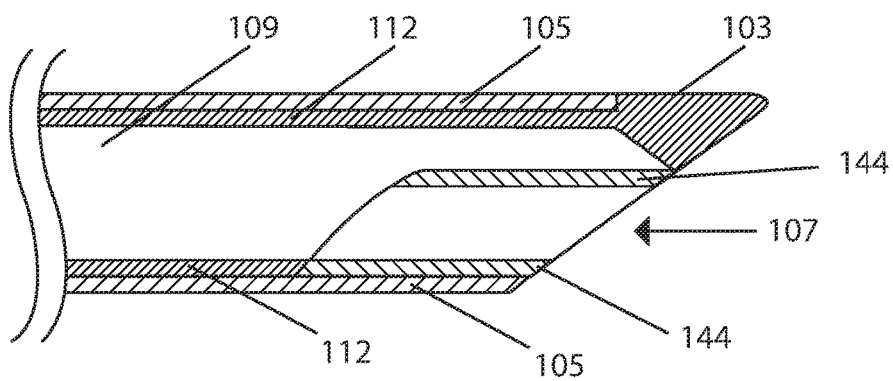
Figure 5C:
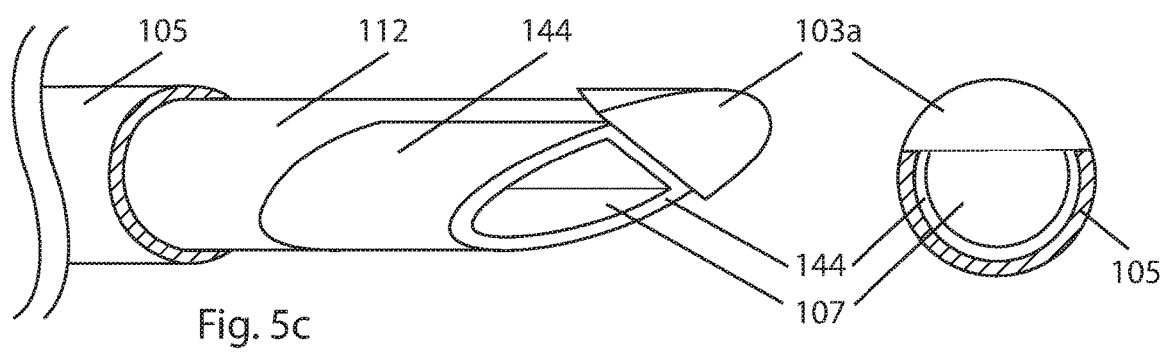

FIGS. 5a to 5c illustrate another embodiment of electrosurgical device 120 wherein the elongate member 102 comprises an electrically conductive tubular member 112 at least partially covered by electrically insulating material 105, the electrically conductive tubular member 112 having a cut away portion proximal of the distal face 104 (of electrosurgical device 120), and the electrosurgical device 120 further comprising an electrically insulating insert 144 located in the cut away portion. The distal face 104 of the electrosurgical device comprises a distal surface of the electrically conductive tubular member defining the at least one cutting portion 103a and a distal surface of the electrically insulating insert 144 defining at least a portion of the at least one non-cutting portion 105a. The distal face 104 of electrosurgical device 120 is beveled. In some alternative embodiments, distal face 104 defines a flat tip. Typically, electrically insulating insert 144 is a polymer. In some embodiments, electrically insulating insert 144 is a stiff plastic, and in some particular embodiments is re-flowed FEP (Fluorinated ethylene propylene). FIG. 5c, which is a rotated side-view, illustrates the device with electrically insulating material 105 partially cut away and shows how electrically conductive tubular member 112 receives electrically insulating insert 144.

FIG. 5b is a cut-away side-view illustrating that electrode 103 extends from electrically conductive tubular member 112. The side-view of FIG. 5a and FIG. 5b show that electrode 103 is an electrically exposed portion of tubular member 112 (i.e. the electrode is continuous with conductive tubular member 112) and is not covered by electrically insulating material 105.

The end view of FIG. 5a shows the electrically insulating insert 144 located between a layer of electrically insulating material 105 and electrode 103. FIGS. 5b and 5c show how electrically insulating insert 144 fits into the cut away portion in electrically conductive tubular member 112, and that insulating material 105 encloses both conductive insert 44 and electrically conductive tubular member 112.

As seen in the FIG. 5a end-view, the electrically insulated portion 105a of distal face 104 is comprised of the end surfaces of both electrically insulating material 105 and electrically insulating insert 144. Electrically exposed conductive portion 103a is comprised of the distal surface of electrode 103. The end views of FIG. 5 show that electrically exposed conductive portion 103a has a shape of a segment of a circle and that electrically insulated portion 105a extends radially from aperture 107 to the periphery 145 of the distal face 104. The electrically insulating insert 144 defines aperture 107. Electrically exposed conductive portion 103a does not fully or partially encircle aperture 107, but instead is lateral to aperture 107, and consequently does not form a ring-shaped electrode capable of coring out tissue.

Figure 6A:
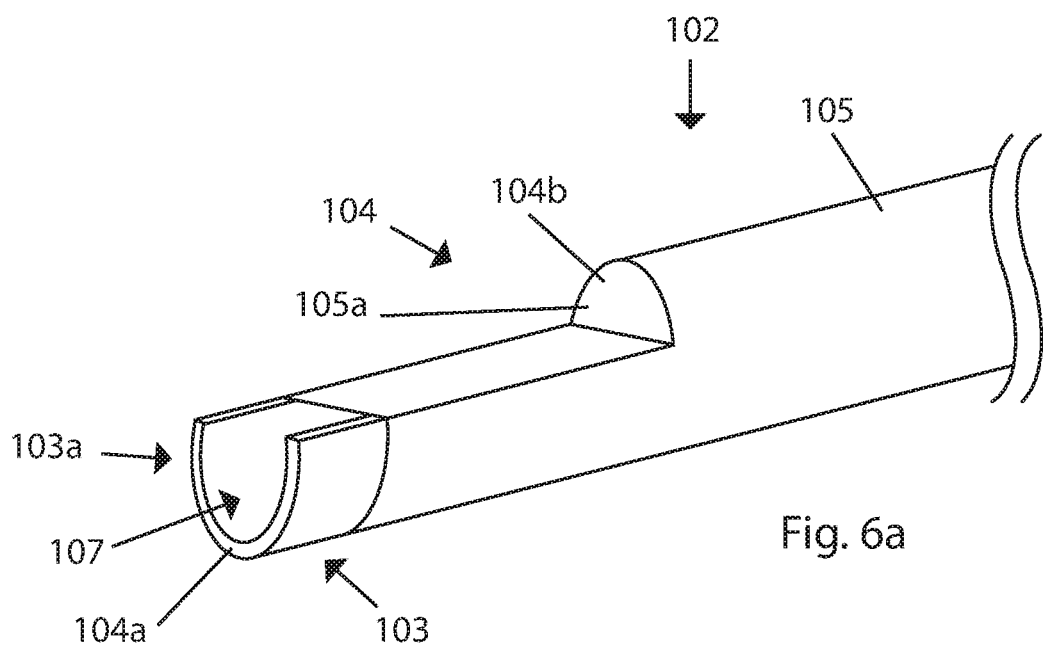
FIGS. 6a and 6b are illustrations of embodiment of a device wherein the distal portion is partially recessed or cut away.

FIGS. 6a and b illustrate embodiments of electrosurgical device 120 wherein a distal end of the elongate member 102 is asymmetrically truncated to define a stepped distal face 104 (of electrosurgical device 120) having a leading portion 104a and a recessed portion 104b. The leading portion 104a includes the cutting portion 103a, and the recessed portion 104b includes the non-cutting portion 105a. In the examples of FIGS. 6a and b, the leading portion 104a is arcuate-shaped. Typically, the elongate member 102 comprises an electrically conductive tubular member at least partially covered by electrically insulating material 105. In some embodiments, non-cutting portion 105a comprises an electrically insulating polymer layer.

In the embodiment of FIG. 6a, recessed portion 104b defines a substantially flat surface comprising non-cutting portion 105a and leading portion 104a defines a flat tip.

Figure 6B:
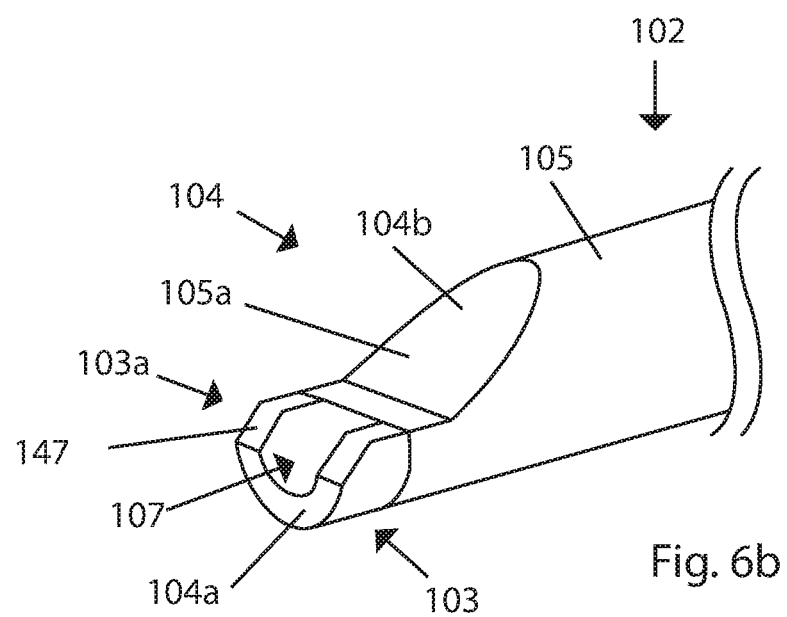

In the embodiment of FIG. 6b, leading portion 104a defines beveled corners 147 and recessed portion 104b defines a sloped surface at least partially defining the at least one non-cutting portion.

In some alternative embodiments (not shown in the drawings), leading portion 104a is beveled.

FIGS. 7a to c illustrate examples of electrosurgical device 120 wherein the at least one cutting portion cutting portion 103a is substantially arcuate and is located along an inner surface of elongate member 102. Typically, the at least one cutting portion 103a comprises an electrically conductive material, the at least one non-cutting portion 105a comprises an electrically insulating layer and is positioned along a distal surface of the elongate member.

In the embodiment of FIG. 7b, cutting portion 103a is crescent-shaped. FIG. 7c illustrates an embodiment wherein distal face 104 is beveled. All of the examples of FIG. 7 have a forward facing aperture 107.

Some alternative embodiments (not shown in figures) include a cutting portion 103a which is embedded in a wall of elongate member 102.

Some other alternative embodiments (not shown in figures) include elongate member 102 comprising an electrically conductive tubular member at least partially covered by an electrically insulating material 105, and the at least one non-cutting portion 105a comprises the electrically insulating material positioned along a portion of a distal surface of the elongate member 102, and wherein an electrically exposed portion of the distal surface of the elongate member 102 forms the at least one cutting portion 103a with the at least one cutting portion being located on the distal face 104 along an inner surface of the elongate member 102 i.e. the cutting portion 103a is adjacent aperture 107 while not extending to the outer periphery of the distal face 104.

In yet some other alternative embodiments, elongate member 102 is comprised of a non-conductive material (e.g. polymer), with the at least one cutting portion 103a being an electrode which is substantially arcuate and located along an inner surface of elongate member 102, and an electrically conductive wire extending to the electrode for supplying electrical power thereto.

Figure 8:
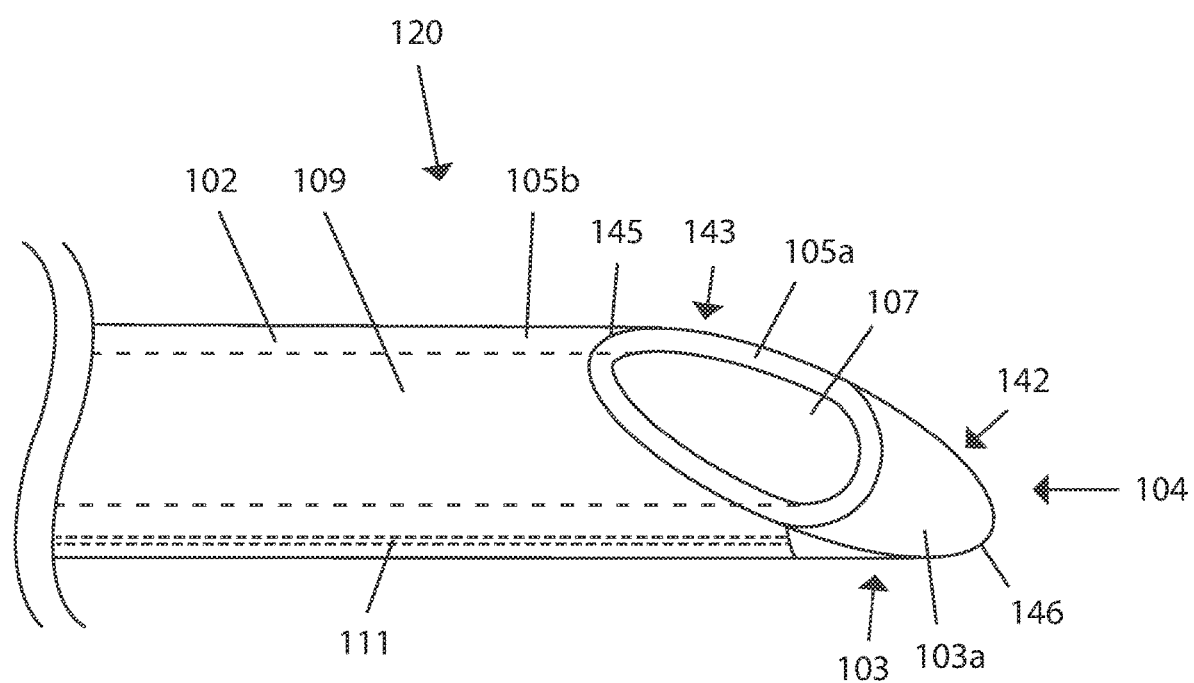
FIG. 8 is an illustration of an embodiment of a surgical device with a non-conductive elongate member.

The embodiment of FIG. 8 is for an electrosurgical device 120 comprising: an elongate member 102 comprising an electrically non-conductive material and defining a lumen 109 for receiving a fluid; a distal face 104 defining an aperture; and the distal face 104 including at least one cutting portion 103a and at least one non-cutting portion 105a configured for cooperating to produce an elongated cut in a tissue when electrical energy is delivered to distal face 104, while avoiding coring of the tissue. A distal end surface of elongate member 102 defines aperture 107. Typically, elongate member 102 is comprised of polymer. In the embodiment of FIG. 8, a distal end surface of electrode 103 is located at a distal end of elongate member 102 and includes the at least one cutting portion 103a. The illustrated embodiment has a beveled distal face 104. In some embodiments, the distal end surface of electrode 103 is crescent shaped, while in some other embodiments, the distal end surface has the shape of a segment of a circle.

In the embodiment of FIG. 8, wire 111 is embedded in a sidewall of elongate member 102 and is connected to electrode 103 for delivering energy thereto. In some alternative embodiments, wire 111 is contained in a lumen of appropriate size.

In the illustrated embodiment, non-cutting portion 105a is located at a proximal portion of distal face 104 and is comprised of the distal surface of elongate member 102. Typically, non-cutting portion 105a is comprised of polymer. When viewed from the end, non-cutting portion 105a encircles aperture 107, while cutting portion 103a does not encircle aperture 107, but instead is lateral to aperture 107, and consequently does not form a ring-shaped electrode capable of coring tissue.

Figure 9A:
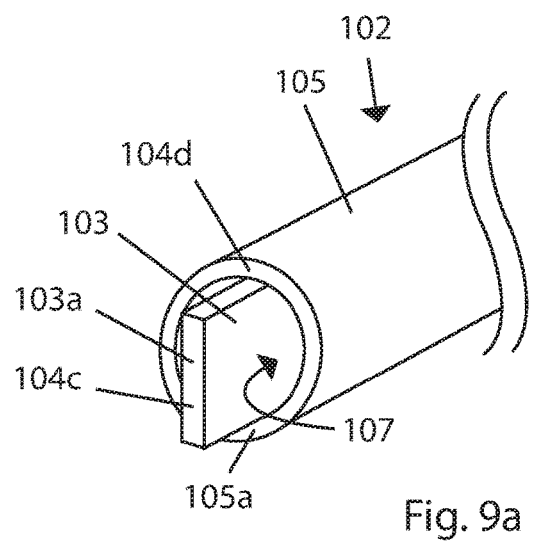
FIGS. 9a and 9b illustrate an embodiment with a rectangular-shaped protruding electrode.
Figure 9B:
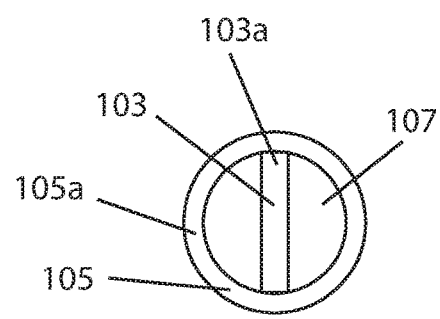
Figure 10A:
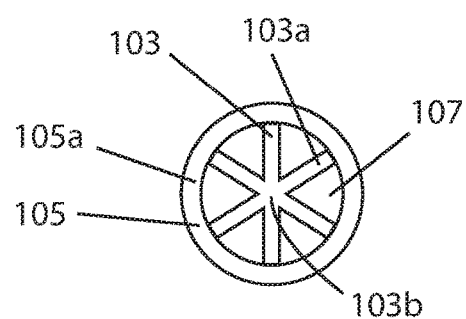
FIGS. 10a and 10b illustrate an embodiment with a star-shaped (or pie cutter-shaped) protruding electrode.
Figure 10B:
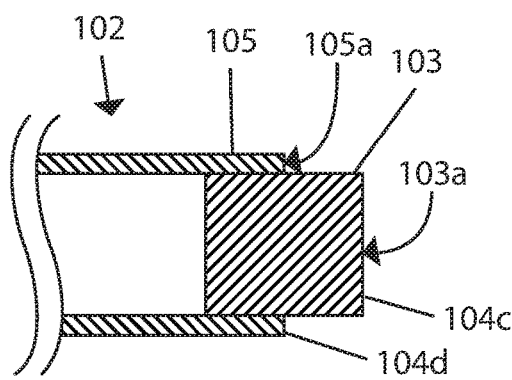

The related embodiments of FIGS. 9 and 10 are for an electrosurgical device 120 comprising a protruding electrode 103 defining a leading surface 104c (FIGS. 9a and 10b) distal of the elongate member 102, with the leading surface 104c including the at least one cutting portion 103a. Distal face 104 comprises a trailing surface 104d (FIGS. 9a and 10b) defined by a distal end surface of the elongate member 102. Trailing surface 104d comprises an electrically insulating material 105 to form non-cutting portion 105a. In some embodiments, leading surface 104c is substantially flat. In some examples, protruding electrode 103 is connected to a rotary mechanism such that the leading surface 104c may be rotated when energy is delivered. Distal face 104 of the electrosurgical device includes leading surface 104c and trailing surface 104d.

In the embodiment of FIGS. 9a and b, protruding electrode 103 substantially bisects the aperture 107 into two parts. The protruding electrode 103, when seen in end view, is substantially rectangular-shaped. In some examples, the leading surface 104c is substantially rectangular-shaped.

Some embodiments of electrosurgical device 120 include the protruding electrode 103 comprising at least three elongate portions radiating from a center point 103b. Some such devices include the protruding electrode 103 substantially dividing the aperture 107 into at least three pie slice shaped wedges. Some embodiments include protruding electrode 103 defining leading surface 104c as having at least three elongate portions radiating from a center point 103b. The example of FIG. 10 has six elongate portions of electrodes 103 radiating from a center point 103b to divide aperture 107 into six wedge-shaped segments. Some embodiments further include the at least three elongate portions of the leading surface 104c sloping proximally as they radiate from the center point 103b.

Some embodiments of FIGS. 9 and 10 include an elongate member 102 comprising an electrically conductive tubular member with an electrically insulating material 105 on the tubular member's distal surface to form non-cutting portion 105a. Some alternative embodiments include elongate member 102 comprising a non-conductive material, for example, polymer.

Figure 14:
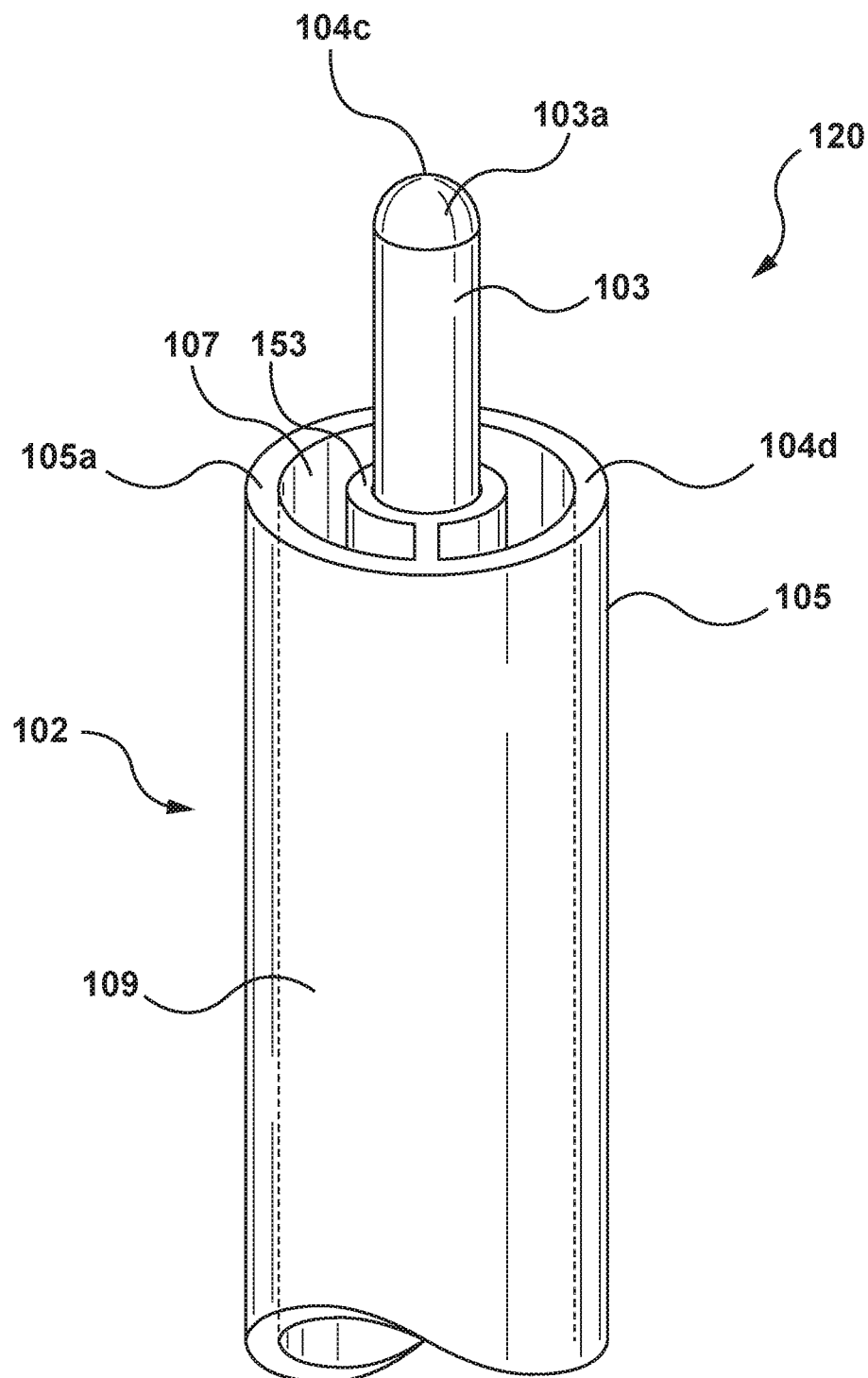
FIG. 14 illustrates an embodiment with a protruding electrode and a support ring.
Figure 15:
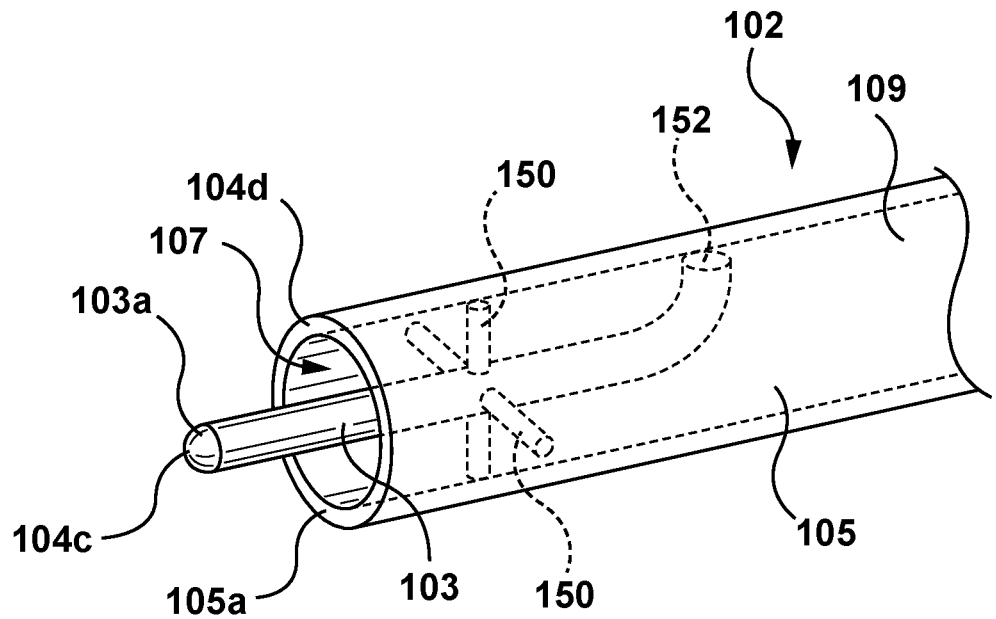
FIG. 15 illustrates an embodiment with a protruding electrode and optional support members.
Figure 16:
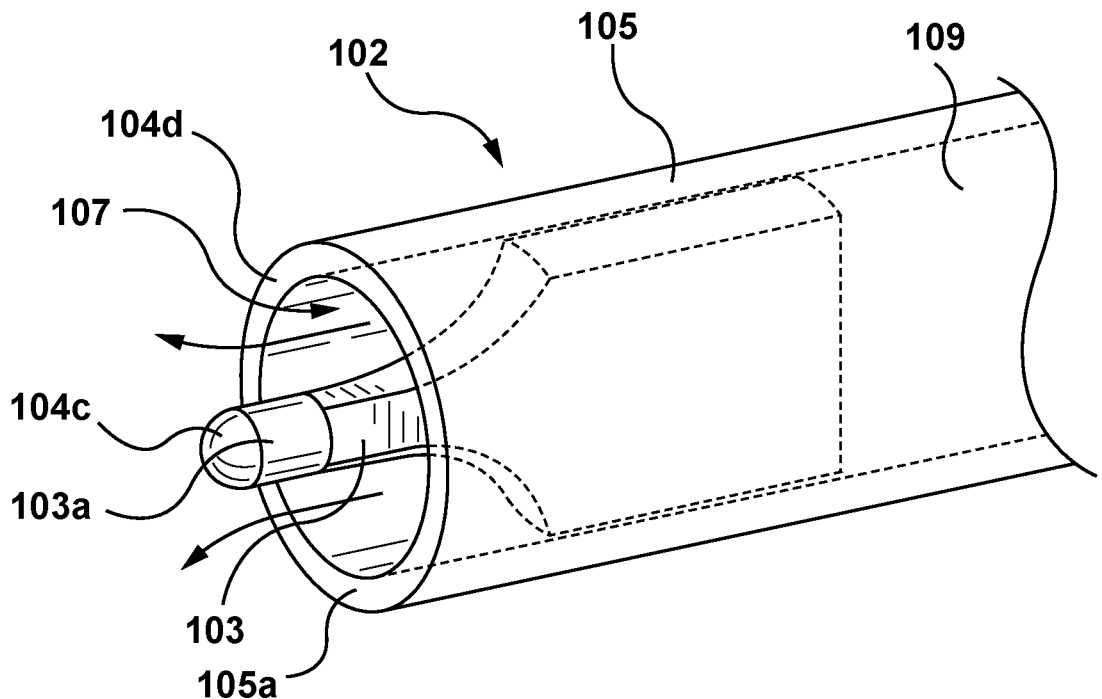
FIG. 16 illustrates an embodiment with a protruding electrode having a widened portion.

The related embodiments of FIGS. 14, 15 and 16 are for an electrosurgical device 120 comprising a protruding electrode 103 defining a leading surface 104c distal of the elongate member 102, with the leading surface 104c including the at least one cutting portion 103a. Distal face 104 comprises a trailing surface 104d defined by a distal end surface of the elongate member 102. Trailing surface 104d comprises an electrically insulating material 105 to form non-cutting portion 105a.

In the embodiment of FIGS. 14, 15 and 16, protruding electrode 103, when seen in end view, is located within aperture 107, leaving the rest of the aperture open. The protruding electrode 103, when seen in end view, may be non-elongated and may have some other configuration, such as, for example, having a circular, square, or rectangular shape.

Correspondingly, the leading surface 104c, when seen in end view, may be non-elongated and may have some other configuration. In some embodiments, leading surface 104c is rounded or domed, while in some alternative embodiments, it is substantially flat.

Typical embodiments of FIGS. 14, 15 and 16 include an elongate member 102 comprising an electrically conductive tubular member with an electrically insulating material 105 on the tubular member's distal surface to form non-cutting portion 105a. Some alternative embodiments include elongate member 102 comprising a non-conductive material, for example, polymer.

The embodiment of FIG. 14 includes a support ring 153 for retaining and supporting electrode 103. In some embodiments, support ring has a limited thickness while in alternative embodiments it persists or extends into the lumen. In some embodiments, support ring 153 is comprised of a non-conductive material and an electrically conductive wire connects electrode 103 to an electrically conductive tubular member. In some alternative embodiments, support ring 153 is comprised of an electrically conductive material, such as metal, with insulation thereupon, with support ring 153 being in electrical communication with an electrically conductive tubular member.

In the embodiment of FIG. 15, the generally J-shaped electrode 103 is connected to an electrically conductive tubular member at point of attachment 152. Optionally, the electrode has some type of stabilizing means, such as, for example, support members 150.

The embodiment of FIG. 16 includes an electrode 103 having a widened portion which is attached to the inner surface of the electrically conductive tubular member along two longitudinal portions of the tube. In the example of FIG. 16, the widened portion has a rectangular shape when seen from an end view or a side view. In the example of FIG. 16, the widened portion is attached proximal of the distal face of the device. In some alternative embodiments, the widened portion is attached adjacent the distal face of the device, whereby the portion of the electrode which increases in width will facilitate dilation of tissue as the device is advanced therethrough.

The embodiments of FIGS. 14, 15 and 16 provide puncturing, dilation, and forward fluid delivery, while avoiding coring. The puncture shape will correspond with the configuration of the electrode's cutting portion 103a and be non-elongate (e.g. circular or square shaped). In more detail, these embodiments include an electrosurgical device for puncturing tissue comprising an elongate member 102 defining a lumen 109 for receiving a fluid; a distal face defining at least one aperture 107; and the distal face including at least one cutting portion 103a and at least one non-cutting portion 105a cooperating to produce a cut in a tissue, which may be non-elongate, when electrical energy is delivered to the distal face, while avoiding coring of the tissue. When energy is delivered through electrode 103 to tissue, the device creates a puncture corresponding with the leading surface 104c with the puncture being surrounded by tissue which the distal face of the device may push aside when the device is advanced.

Figure 11:
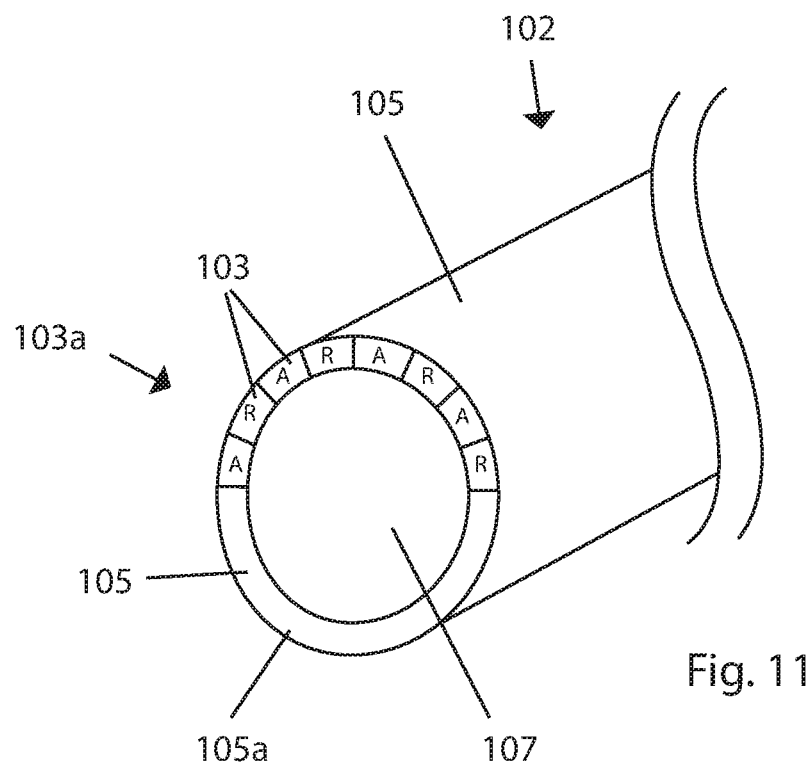
FIG. 11 illustrates a bi-polar embodiment with peripheral cutting electrodes.

The embodiment of the electrosurgical device of FIG. 11 includes the at least one cutting portion 103a being arcuate-shaped and partially surrounding aperture 107, with the at least one cutting portion 103a comprising at least one active electrode 103 (indicated by "A" in FIG. 11) and at least one return electrode 103 (indicated by "R" in FIG. 11) being operable for bi-polar energy delivery. Typically, embodiments have pairs of electrodes, one active and one return, whereby typical embodiments have 2, 4, 8, 10 or more electrodes.

In some embodiments, such as the example of FIG. 11, cutting portion 103a comprises a 180 degree arc of a circle. Cutting portion 103a of FIG. 11 includes four active electrodes and four return electrodes arranged in an alternating pattern.

In typical embodiments, non-cutting portion 105a comprises an electrically insulating material 105.

Figure 12:
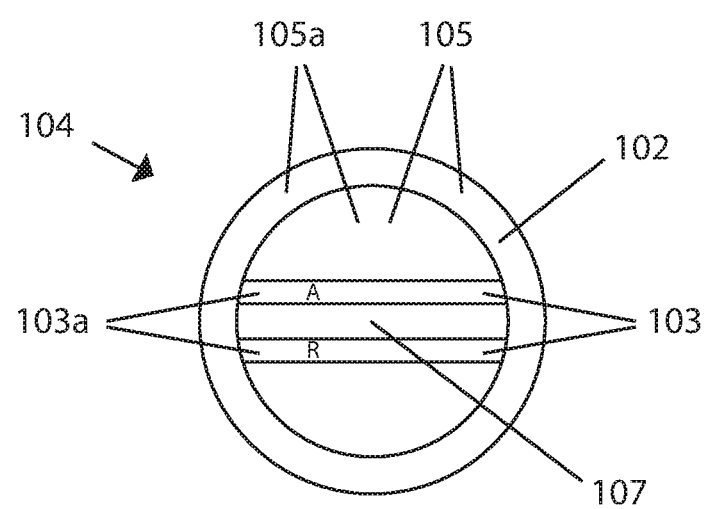
FIG. 12 illustrates a bi-polar embodiment with central transverse cutting.

The example illustrated in FIG. 12 is for another bi-polar device. The electrosurgical device of FIG. 12 includes the at least one cutting portion 103a comprising an active electrode 103 (indicated by "A" in FIG. 12) and a return electrode 103 (indicated by "B" in FIG. 12) parallel to one another and substantially extending across the aperture 107, the active electrode and the return electrode being operable for bi-polar energy delivery. In typical embodiments, the aperture 107 is between the active electrode and the return electrode, as shown in the drawing.

In some embodiments, the portion of the distal face 104 between the active electrode and the elongate member 102, and the portion of the distal face between the return electrode and the elongate member 102, are both comprised of electrically insulating material 105. In the embodiment of FIG. 12, the aforementioned electrically insulating material 105 between the electrodes and the elongate member 102 and electrically insulating material 105 at the distal surface, together, form non-cutting portion 105a. The distal face 104 of the electrosurgical device includes the above described cutting portion 103a and non-cutting portion 105a.

Figure 13A:
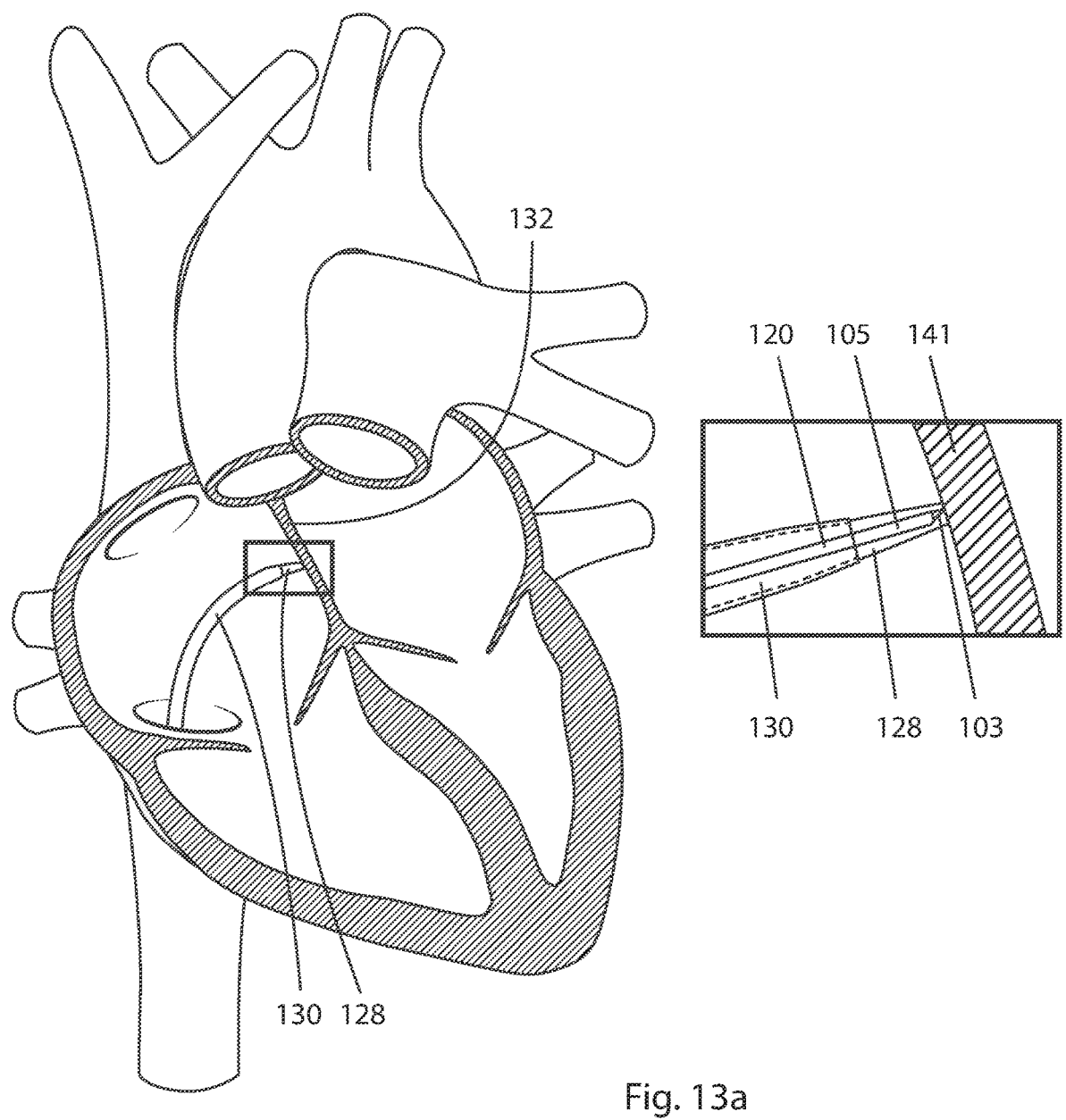
FIGS. 13a and 13b illustrate an embodiment of a method of puncturing tissue within a heart.
Figure 13B:
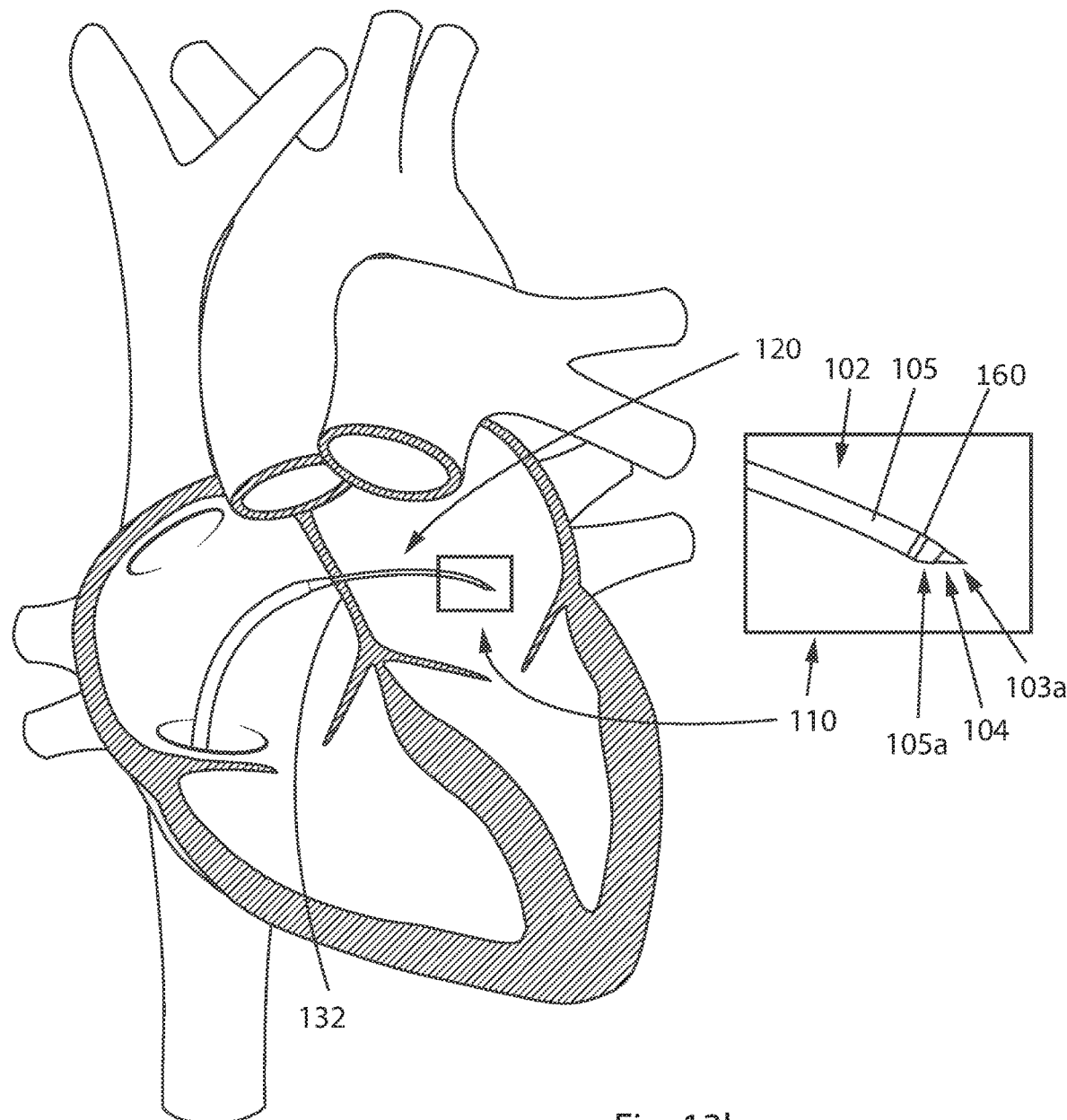

FIGS. 13a and 13b illustrate an embodiment of a method of puncturing tissue. The method comprises the steps of (a) delivering energy through electrically exposed conductive portion 103a of electrosurgical device 120 to tissue 141 at a target site for creating a puncture substantially corresponding to an elongate cutting portion of the distal face of the electrosurgical device; and (b) dilating or widening the puncture primarily by advancing a flat-tipped or angled distal surface of the electrosurgical device, without coring the tissue. In some embodiments the step of delivering energy comprises creating a flap in the tissue and the step of dilating or widening is completed without further delivery of energy. In some embodiments, the target site is a tissue within a heart, and in some particular embodiments the tissue is an atrial septum 132. Typically, the method uses a sheath, for example, sheath 130 of FIG. 7a. The term dilate is used herein to mean "to make wider, larger, or more open".

An alternative embodiment of a method of puncturing tissue comprises the steps of (a) delivering energy through a cutting portion a distal face of an electrosurgical device to tissue at a target site to create an elongate puncture through the tissue, while preventing delivery of energy from a non-cutting portion of the distal face; and (b) advancing the electrosurgical device through the tissue by pushing aside a flap of tissue defined by the puncture. The step of delivering energy comprises creating a slit or slits (e.g. using the FIG. 10 embodiment) in the tissue.

Dilating the puncture typically includes displacing the tissue. In some embodiments dilation includes wedging apart and thereby outwardly compressing surrounding portions of the tissue.

Some embodiments of the method include using a medical imaging modality to guide the electrosurgical device 120 to the target site. Some embodiments comprise measuring pressure for positioning electrosurgical device 120 at the target site. In some embodiments, the method includes using a radiopaque marker 160 for positioning electrosurgical device 120. Some embodiments include advancing the electrosurgical device to the target site over a guide-wire.

In some embodiments, the method includes advancing electrosurgical device 120 to the target site through a dilator 128; positioning electrosurgical device 120 such that cutting portion 103a is aligned with or protruding slightly from a distal end of the dilator 128; and delivering fluid through an aperture 107 (e.g. FIG. 3) at a distal end of electrosurgical device 120 to stain the tissue. The fluid is typically delivered longitudinally forward through the electrosurgical device. Some embodiments further comprise a step of withdrawing a fluid via an open distal face of the electrosurgical device.

In some embodiments, the distal surface of the electrically exposed conductive portion 103a is generally C-shaped and step (b) includes creating a generally C-shaped puncture. In some other embodiments, the distal surface of the electrically exposed conductive portion is generally crescent-shaped and step (b) includes creating a generally crescent-shaped puncture. In yet other embodiments, the distal surface of the electrically exposed conductive portion is generally arcuate-shaped and step (b) includes creating a generally arcuate-shaped puncture.

In some embodiments of the broad aspect, the aperture 107 and the lumen 109 together comprise a pressure transmitting lumen, and the method further comprises measuring a fluid pressure of the pressure transmitting lumen using a pressure sensing mechanism.

In an RF perforation or puncturing procedure, unlike RF ablation, energy is applied to rapidly increase tissue temperature to the extent that the intracellular fluid becomes converted to steam, inducing cell lysis as a result of elevated pressure within the cell. Upon the occurrence of cell lysis and rupture, a void is created, allowing the tip of the catheter to penetrate the tissue. In order to achieve this effect, RF perforation devices must apply a high voltage to the tissue region over a short period of time. Also, the tip of the device being used should be relatively small, in order to increase the impedance of the device. This is in contrast to RF ablation, whereby a larger-tipped device is utilized to deliver a low impedance and high power signal to the region involved. Furthermore, as opposed to RF perforation, which creates a void in the tissue through which the device may be advanced, the objective of RF ablation is to create a large, non-penetrating lesion in the tissue, in order to disrupt electrical conduction. Thus, for the purposes of the present invention, perforation is defined as the creation of a void within a material.

Embodiments of the present invention are operable to create such punctures or voids without substantially removing a plug or core of material from the tissue at the target site, since the puncture resulting from devices as described hereinabove are typically slit-like, C-shaped, or similar configurations substantially corresponding to the shape(s) of the cutting portion of the distal face of the electrosurgical device.

Electrosurgical device 120 may be used in conjunction with a source of radiofrequency energy suitable for perforating material within a patient's body. The source of energy may be a radiofrequency (RF) electrical generator, operable in the range of about 100 kHz to about 1000 kHz, and designed to generate a high voltage over a short period of time. More specifically, in some embodiments, the voltage generated by the generator increases from about 0 V (peak-to-peak) to greater than about 75 V (peak-to-peak) in less than about 0.6 seconds. The maximum voltage generated by generator may be between about 180V peak-to-peak and about 3000V peak-to-peak. The waveform generated may vary, and may include, for example, a sine-wave, a rectangular-wave, or a pulsed rectangular wave, amongst others. During delivery of radiofrequency energy, the impedance load may increase due to tissue lesioning near the target-site, or the formation of a vapor layer following cell rupture, for example. The generator may be operable to continue to increase the voltage, even as the impedance load increases. For example, energy may be delivered to a tissue within a body at a voltage that rapidly increases from about 0 V (RMS) to about 220 V (RMS) for a period of between about 0.5 seconds and about 5 seconds.

Without being limited to a particular theory of operation, it is believed that under particular circumstances, for example as mentioned hereinabove, dielectric breakdown and arcing may occur upon the delivery of radiofrequency energy, whereby polar molecules may be pulled apart. The combination of these factors may result in the creation of an insulative vapor layer around the electrode, therein resulting in an increase in impedance, for example the impedance may increase to greater than 4000Ω. In some embodiments, despite this high impedance, the voltage continues to increase. Further increasing the voltage increases the intensity of fulguration, which may be desirable as it allows for an increased perforation rate and puncture creation. An example of an appropriate generator for this application is the BMC RF Perforation Generator (model number RFP-100A, Baylis Medical Company, Montreal, Canada) This generator delivers continuous RF energy at about 460 kHz.

A grounding pad or dispersive electrode may be electrically coupled to the generator for contacting or attaching to the body of the patient to provide a return path for the RF energy when the generator is operated in a monopolar mode.

Additional details regarding the device and method may be found in U.S. application Ser. No. 13/468,939, filed May 10, 2012, U.S. application Ser. No. 11/905,447, filed Oct. 1, 2007 (now issued as U.S. Pat. No. 8,192,425), U.S. application Ser. No. 13/113,326, filed May 23, 2007, U.S. application Ser. No. 11/265,304, filed Nov. 3, 2005 (now U.S. Pat. No. 7,947,040), U.S. application Ser. No. 10/666,301, filed Sep. 19, 2003 (now issued as U.S. Pat. No. 7,048,733), U.S. application Ser. No. 10/760,479, filed Jan. 21, 2004 (now issued as U.S. Pat. No. 7,270,662), U.S. application Ser. No. 10/666,288, filed Sep. 19, 2003, U.S. application Ser. No. 10/347,366, filed Jan. 21, 2003 (now issued as U.S. Pat. No. 7,112,197), U.S. provisional application Ser. No. 60/522,753, filed Nov. 3, 2004, and provisional application Ser. No. 60/884,285, filed Jan. 10, 2007, 60/827,452, filed Sep. 29, 2006, Ser. No. 61/653,967, filed May 31, 2012, and Ser. No. 61/681,512, filed Aug. 9, 2012. The contents of all above-named applications and patents are incorporated herein by reference in their entirety.

Thus, as described hereinabove, the problem of puncturing tissue without coring, while providing forward fluid delivery, is solved by an electrosurgical device comprising a distal face defining at least one aperture, and the distal face including at least one cutting portion and at least one non-cutting portion cooperating to produce an elongated cut in a tissue when electrical energy is delivered to the distal face, while avoiding coring of the tissue.

Example 1

Embodiments having the configuration of FIG. 2 were tested and found to puncture tissue substantially without coring. Electrified Brockenbrough needles were also tested, and found to core tissue when puncturing. The testing revealed that FIG. 2 embodiments cut C-shaped punctures that correspond to the shape of the electrode when viewed from the end, resulting in a flap of skin that is displaced sideways by the proximal portion of distal face 104 when electrosurgical device 120 is advanced, whereby the C-shaped puncture is dilated.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. An electrosurgical device for puncturing a tissue comprising:
   an elongate member having a longitudinal axis and defining a lumen for fluid;
   a distal portion which includes an electrode and a distal face;
   the distal face defining at least one aperture;
   the distal face including at least one non-cutting portion and at least one cutting portion configured to deliver energy for puncturing the tissue wherein a distal surface of the electrode forms the at least one cutting portion;
   a portion of the at least one cutting portion defining a leading portion partially surrounding a circumference of the at least one aperture and at least a portion of the at least one cutting portion defines a flat tip having a planar surface perpendicular to the longitudinal axis of the elongate member along both non-longitudinal axes; and
   wherein an outer diameter of at least one of the distal portion of the electrosurgical device or the electrode decreases towards a distal tip of the electrosurgical device, and an entirety of the non-cutting portion is recessed relative to the leading portion.

2. The electrosurgical device of claim 1 wherein the elongate member is comprised of an electrically conductive tube at least partially covered by an electrically insulating material and wherein an electrically exposed portion of the distal face of the elongate member forms the at least one cutting portion.

3. The electrosurgical device of claim 2, wherein the at least one non-cutting portion comprises the electrically insulating material.

4. The electrosurgical device of claim 3, wherein the decreases towards the distal tip of the electrosurgical device comprises a gradual sloped portion to the at least one cutting portion.

5. The electrosurgical device of claim 4, wherein the at least one non-cutting portion is defined by the gradual sloped portion.

6. The electrosurgical device of claim 5, wherein the at least one cutting portion is configured to produce an elongated cut in the tissue whereby the elongated cut avoids coring of the tissue.

7. The electrosurgical device of claim 6, wherein the gradual sloped portion is configured to dilate tissue as the electrosurgical device is advanced through the elongated cut.

8. The electrosurgical device of claim 3, wherein the leading portion is annular.

9. The electrosurgical device of claim 8, wherein the at least one cutting portion further comprises at least one beveled corner which meets with the electrically insulating material.

10. The electrosurgical device of claim 3, wherein the at least one cutting portion comprises a notch extending axially along a length of the distal portion of the elongate member.

11. The electrosurgical device of claim 3, wherein the at least one aperture is enclosed by the at least one cutting portion and the electrically insulating material.

12. The electrosurgical device of claim 1, wherein the at least one cutting portion has a smaller cross-sectional area than a cross-sectional area of a distal end of the elongate member.

13. The electrosurgical device of claim 1, wherein the elongate member is comprised of electrically conductive material such that energy is delivered along its length to the electrode.

* * * * *